(12) United States Patent
Hatch

(10) Patent No.: US 8,114,156 B2
(45) Date of Patent: Feb. 14, 2012

(54) FLEXIBLY COMPLIANT CERAMIC PROSTHETIC MENISCUS FOR THE REPLACEMENT OF DAMAGED CARTILAGE IN ORTHOPEDIC SURGICAL REPAIR OR RECONSTRUCTION OF HIP, KNEE, ANKLE, SHOULDER, ELBOW, WRIST AND OTHER ANATOMICAL JOINTS

(76) Inventor: Edwin Burton Hatch, The Villages, FL (US)

(*) Notice: Subject to any disclaimer, the term of this patent is extended or adjusted under 35 U.S.C. 154(b) by 144 days.

(21) Appl. No.: 12/381,566

(22) Filed: Mar. 12, 2009

(65) Prior Publication Data
US 2010/0168857 A1 Jul. 1, 2010

Related U.S. Application Data

(60) Provisional application No. 61/130,279, filed on May 30, 2008, provisional application No. 61/192,848, filed on Sep. 23, 2008.

(51) Int. Cl.
*A61F 2/08* (2006.01)
(52) U.S. Cl. .................................... 623/14.12
(58) Field of Classification Search ............... 623/11.11, 623/13.11–13.2, 14.12, 16.11, 17.11–17.19, 623/20.16, 23.56; 606/90–94, 246–249, 606/99
See application file for complete search history.

(56) References Cited

U.S. PATENT DOCUMENTS

| | | | | |
|---|---|---|---|---|
| 3,605,123 A * | 9/1971 | Hahn | ............... | 623/23.55 |
| 3,715,763 A * | 2/1973 | Link | ............... | 623/20.3 |
| 3,720,996 A * | 3/1973 | Tschermak | ............... | 29/527.1 |
| 3,774,244 A * | 11/1973 | Walker | ............... | 623/20.3 |
| 3,855,638 A * | 12/1974 | Pilliar | ............... | 623/23.55 |
| 3,867,728 A * | 2/1975 | Stubstad et al. | ............... | 623/17.16 |
| 4,195,368 A * | 4/1980 | Patrichi | ............... | 623/14.12 |
| 4,213,816 A * | 7/1980 | Morris | ............... | 156/245 |
| 4,344,193 A * | 8/1982 | Kenny | ............... | 623/14.12 |
| 4,454,621 A * | 6/1984 | Testone | ............... | 15/1.51 |
| 4,479,271 A * | 10/1984 | Bolesky et al. | ............... | 623/20.17 |
| 4,501,031 A * | 2/1985 | McDaniel et al. | ............... | 623/20.32 |
| 4,502,161 A * | 3/1985 | Wall | ............... | 623/14.12 |
| 4,636,219 A * | 1/1987 | Pratt et al. | ............... | 623/23.3 |
| 4,731,086 A * | 3/1988 | Whiteside et al. | ............... | 623/20.16 |
| 4,795,468 A * | 1/1989 | Hodorek et al. | ............... | 623/20.28 |
| 4,919,667 A * | 4/1990 | Richmond | ............... | 623/14.12 |
| 4,991,667 A * | 2/1991 | Wilkes et al. | ............... | 175/61 |
| 4,997,445 A * | 3/1991 | Hodorek | ............... | 623/23.51 |
| 5,007,934 A * | 4/1991 | Stone | ............... | 623/14.12 |
| 5,047,057 A * | 9/1991 | Lawes | ............... | 623/20.29 |
| 5,092,894 A * | 3/1992 | Kenny | ............... | 128/898 |
| 5,171,322 A * | 12/1992 | Kenny | ............... | 623/14.12 |
| 5,175,710 A * | 12/1992 | Hutson | ............... | 367/135 |
| 5,201,881 A * | 4/1993 | Evans | ............... | 623/20.28 |
| 5,281,422 A * | 1/1994 | Badylak et al. | ............... | 623/13.11 |
| 5,306,311 A * | 4/1994 | Stone et al. | ............... | 623/14.12 |
| 5,314,478 A * | 5/1994 | Oka et al. | ............... | 623/14.12 |
| 5,344,459 A * | 9/1994 | Swartz | ............... | 623/14.12 |
| 5,358,525 A * | 10/1994 | Fox et al. | ............... | 623/14.12 |
| 5,358,529 A * | 10/1994 | Davidson | ............... | 623/20.19 |

(Continued)

*Primary Examiner* — Alvin J Stewart

(57) ABSTRACT

A flexibly compliant ceramic prosthetic meniscus comprised of ceramic fibers formed into a rope-like structure. The rope-like structure is coiled into a pad configuration with the proximal and distal ends completely placed into an interior of the pad to create a more stabilized structure. A flexibly compliant ceramic prosthetic meniscus fixed together by being sewn together using a high melting temperature ceramic thread. A flexibly compliant ceramic fiber prosthetic fixed together by being thermally fused. A flexibly compliant ceramic fiber prosthetic meniscus is thermally fused onto a metal prosthesis of the said patient's articulating joint. A flexibly compliant ceramic fiber prosthetic meniscus is bonded onto a metal prosthesis of the said patient's articulating joint.

5 Claims, 22 Drawing Sheets

Section A-A

U.S. PATENT DOCUMENTS

| | | | | |
|---|---|---|---|---|
| 5,380,328 | A * | 1/1995 | Morgan | 606/70 |
| 5,397,365 | A * | 3/1995 | Trentacosta | 623/18.11 |
| 5,609,645 | A * | 3/1997 | Vinciguerra | 623/20.28 |
| 5,662,158 | A * | 9/1997 | Caldarise | 164/456 |
| 5,716,416 | A * | 2/1998 | Lin | 623/17.16 |
| 5,919,235 | A * | 7/1999 | Husson et al. | 623/17.16 |
| 5,944,759 | A * | 8/1999 | Link | 623/18.11 |
| 5,976,186 | A * | 11/1999 | Bao et al. | 623/17.16 |
| 6,027,744 | A * | 2/2000 | Vacanti et al. | 424/426 |
| 6,264,695 | B1 * | 7/2001 | Stoy | 623/17.16 |
| 6,280,475 | B1 * | 8/2001 | Bao et al. | 623/17.16 |
| 6,280,478 | B1 * | 8/2001 | Richter et al. | 623/23.56 |
| 6,558,421 | B1 * | 5/2003 | Fell et al. | 623/14.12 |
| 6,592,622 | B1 * | 7/2003 | Ferguson | 623/13.14 |
| 6,607,505 | B1 * | 8/2003 | Thompson et al. | 604/95.04 |
| 6,610,094 | B2 * | 8/2003 | Husson | 623/17.16 |
| 6,613,046 | B1 * | 9/2003 | Jenkins et al. | 606/41 |
| 6,620,196 | B1 * | 9/2003 | Trieu | 623/17.16 |
| 6,629,997 | B2 * | 10/2003 | Mansmann | 623/14.12 |
| 6,632,246 | B1 * | 10/2003 | Simon et al. | 623/14.12 |
| 6,679,914 | B1 * | 1/2004 | Gabbay | 623/14.12 |
| 6,712,853 | B2 * | 3/2004 | Kuslich | 623/17.16 |
| 6,752,831 | B2 * | 6/2004 | Sybert et al. | 623/13.17 |
| 6,827,743 | B2 * | 12/2004 | Eisermann et al. | 623/23.54 |
| 6,872,227 | B2 * | 3/2005 | Sump et al. | 623/13.2 |
| 6,893,466 | B2 * | 5/2005 | Trieu | 623/17.16 |
| 6,913,622 | B2 * | 7/2005 | Gjunter | 623/17.16 |
| 6,966,928 | B2 * | 11/2005 | Fell et al. | 623/14.12 |
| 7,004,971 | B2 * | 2/2006 | Serhan et al. | 623/17.16 |
| 7,144,425 | B2 * | 12/2006 | Steiner et al. | 623/13.14 |
| 7,204,851 | B2 * | 4/2007 | Trieu et al. | 623/17.11 |
| 7,291,169 | B2 * | 11/2007 | Hodorek | 623/14.12 |
| 7,476,250 | B1 * | 1/2009 | Mansmann | 623/14.12 |
| 7,531,004 | B2 * | 5/2009 | Bagga et al. | 623/23.51 |
| 7,534,451 | B2 * | 5/2009 | Erbe et al. | 424/484 |
| 7,537,617 | B2 * | 5/2009 | Bindsell et al. | 623/17.16 |
| 7,731,756 | B2 * | 6/2010 | Maspero et al. | 623/23.51 |
| 7,758,643 | B2 * | 7/2010 | Stone et al. | 623/14.12 |
| 7,758,647 | B2 * | 7/2010 | Arnin et al. | 623/17.16 |
| 7,785,368 | B2 * | 8/2010 | Schaller | 623/17.11 |
| 7,803,188 | B2 * | 9/2010 | Justis et al. | 623/17.11 |
| 7,819,918 | B2 * | 10/2010 | Malaviya et al. | 623/14.12 |
| 7,887,593 | B2 * | 2/2011 | McKay et al. | 623/17.16 |
| 7,892,291 | B2 * | 2/2011 | Evans et al. | 623/23.51 |
| 7,901,460 | B2 * | 3/2011 | Sherman | 623/17.16 |
| 7,955,391 | B2 * | 6/2011 | Schaller | 623/17.11 |
| 7,967,864 | B2 * | 6/2011 | Schaller | 623/17.11 |
| 7,988,735 | B2 * | 8/2011 | Yurek et al. | 623/17.12 |
| 7,998,204 | B2 * | 8/2011 | Stone et al. | 623/13.18 |
| 8,012,211 | B2 * | 9/2011 | Kuslich | 623/17.12 |
| 8,016,884 | B2 * | 9/2011 | Shterling et al. | 623/14.12 |
| 2002/0091444 | A1 * | 7/2002 | Yang | 623/11.11 |
| 2002/0123750 | A1 * | 9/2002 | Eisermann et al. | 606/69 |
| 2002/0183845 | A1 * | 12/2002 | Mansmann | 623/13.11 |
| 2002/0183857 | A1 * | 12/2002 | Yang | 623/23.72 |
| 2003/0036797 | A1 * | 2/2003 | Malaviya et al. | 623/14.12 |
| 2004/0133275 | A1 * | 7/2004 | Mansmann | 623/14.12 |
| 2004/0199250 | A1 * | 10/2004 | Fell | 623/14.12 |
| 2004/0260397 | A1 * | 12/2004 | Lambrecht et al. | 623/17.16 |
| 2004/0267362 | A1 * | 12/2004 | Hwang et al. | 623/13.15 |
| 2004/0267363 | A1 * | 12/2004 | Fell et al. | 623/14.12 |
| 2005/0177240 | A1 * | 8/2005 | Blain | 623/17.15 |
| 2005/0209703 | A1 * | 9/2005 | Fell | 623/20.33 |
| 2005/0214340 | A1 * | 9/2005 | Erbe et al. | 424/423 |
| 2005/0221703 | A1 * | 10/2005 | Stone | 442/123 |
| 2005/0222687 | A1 * | 10/2005 | Vunjak-Novakovic et al. | 623/23.63 |
| 2005/0234549 | A1 * | 10/2005 | Kladakis et al. | 623/14.12 |
| 2005/0261736 | A1 * | 11/2005 | Murray et al. | 606/214 |
| 2005/0261767 | A1 * | 11/2005 | Anderson et al. | 623/16.11 |
| 2005/0278025 | A1 * | 12/2005 | Ku et al. | 623/14.12 |
| 2006/0173542 | A1 * | 8/2006 | Shikinami | 623/14.12 |
| 2006/0190078 | A1 * | 8/2006 | Fell | 623/14.12 |
| 2006/0241756 | A1 * | 10/2006 | Fritz et al. | 623/14.12 |
| 2007/0050038 | A1 * | 3/2007 | Snell et al. | 623/17.16 |
| 2007/0065943 | A1 * | 3/2007 | Smith et al. | 435/395 |
| 2007/0067032 | A1 * | 3/2007 | Felt et al. | 623/14.12 |
| 2007/0073394 | A1 * | 3/2007 | Seedhom et al. | 623/14.12 |
| 2007/0083266 | A1 * | 4/2007 | Lang | 623/17.11 |
| 2007/0100450 | A1 * | 5/2007 | Hodorek | 623/14.12 |
| 2007/0113951 | A1 * | 5/2007 | Huang | 156/89.11 |
| 2007/0179606 | A1 * | 8/2007 | Huyghe et al. | 623/14.12 |
| 2007/0179607 | A1 * | 8/2007 | Hodorek et al. | 623/14.12 |
| 2007/0250164 | A1 * | 10/2007 | Troxel | 623/14.12 |
| 2007/0270969 | A1 * | 11/2007 | Schmid | 623/17.11 |
| 2008/0051800 | A1 * | 2/2008 | Diaz et al. | 606/92 |
| 2008/0051889 | A1 * | 2/2008 | Hodorek | 623/14.12 |
| 2008/0058952 | A1 * | 3/2008 | Trieu et al. | 623/23.48 |
| 2008/0086210 | A1 * | 4/2008 | Fox | 623/14.12 |
| 2008/0091199 | A1 * | 4/2008 | Cragg | 606/60 |
| 2008/0097605 | A1 * | 4/2008 | Pastorello et al. | 623/14.12 |
| 2008/0119930 | A1 * | 5/2008 | Osada et al. | 623/14.12 |
| 2008/0132899 | A1 * | 6/2008 | Shadduck et al. | 606/94 |
| 2008/0154370 | A1 * | 6/2008 | Mathies | 623/14.12 |
| 2008/0234827 | A1 * | 9/2008 | Schaller et al. | 623/17.16 |
| 2008/0275555 | A1 * | 11/2008 | Makower et al. | 623/14.12 |
| 2008/0294171 | A1 * | 11/2008 | Boehm et al. | 606/90 |
| 2008/0306595 | A1 * | 12/2008 | McLeod et al. | 623/17.16 |
| 2009/0012616 | A1 * | 1/2009 | James et al. | 623/17.11 |
| 2009/0012621 | A1 * | 1/2009 | James et al. | 623/17.16 |
| 2009/0030523 | A1 * | 1/2009 | Taylor | 623/17.16 |
| 2009/0048677 | A1 * | 2/2009 | McLeod et al. | 623/17.16 |
| 2009/0088846 | A1 * | 4/2009 | Myung et al. | 623/14.12 |
| 2009/0118830 | A1 * | 5/2009 | Fell | 623/14.12 |
| 2009/0132047 | A1 * | 5/2009 | Mansmann et al. | 623/14.12 |
| 2009/0155334 | A1 * | 6/2009 | Mallick et al. | 424/423 |
| 2009/0192609 | A1 * | 7/2009 | Klabunde et al. | 623/16.11 |
| 2009/0226068 | A1 * | 9/2009 | Fitz et al. | 382/131 |
| 2009/0259312 | A1 * | 10/2009 | Shterling et al. | 623/14.12 |
| 2009/0291112 | A1 * | 11/2009 | Truncale et al. | 424/423 |
| 2009/0299474 | A1 * | 12/2009 | Branch et al. | 623/16.11 |
| 2009/0306778 | A1 * | 12/2009 | Marvel | 623/14.12 |
| 2010/0114316 | A1 * | 5/2010 | Swords | 623/16.11 |
| 2010/0151114 | A1 * | 6/2010 | Parrott | 427/2.26 |
| 2010/0168856 | A1 * | 7/2010 | Long et al. | 623/14.12 |
| 2010/0168857 | A1 * | 7/2010 | Hatch | 623/14.12 |
| 2010/0262242 | A1 * | 10/2010 | Chavatte et al. | 623/17.12 |
| 2010/0286778 | A1 * | 11/2010 | Eisermann et al. | 623/17.11 |
| 2011/0066243 | A1 * | 3/2011 | Rivin et al. | 623/14.12 |
| 2011/0093073 | A1 * | 4/2011 | Gatt et al. | 623/14.12 |

* cited by examiner

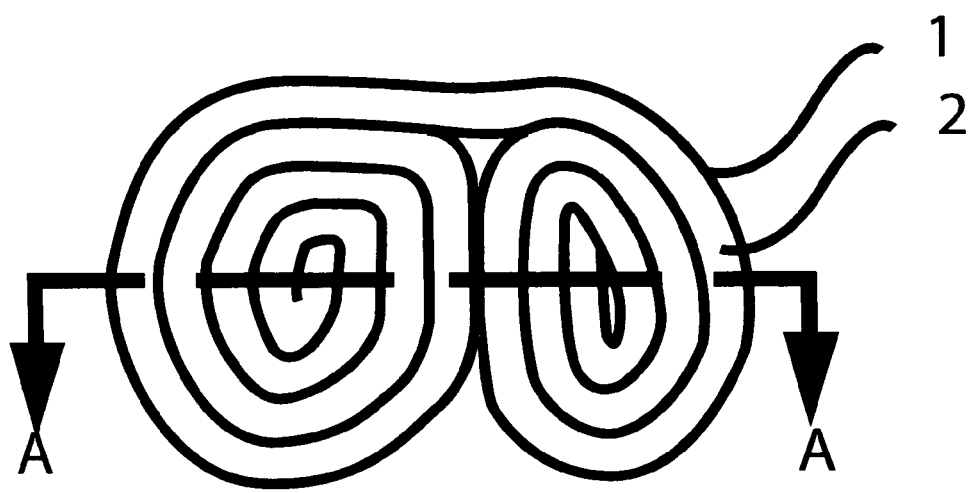
FIG. 1
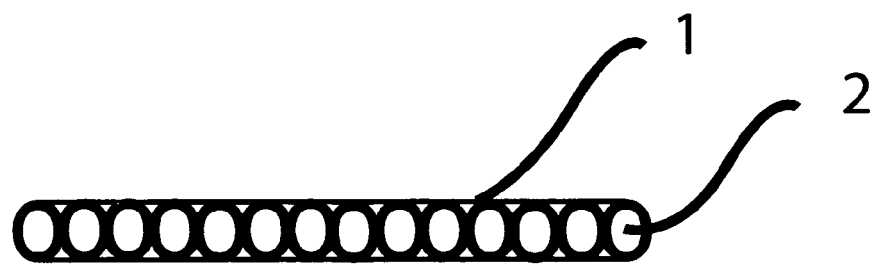
Section A-A

— 1
— 2
— 3

— 1
— 2
— 3
— 4

— 1
— 2
— 5

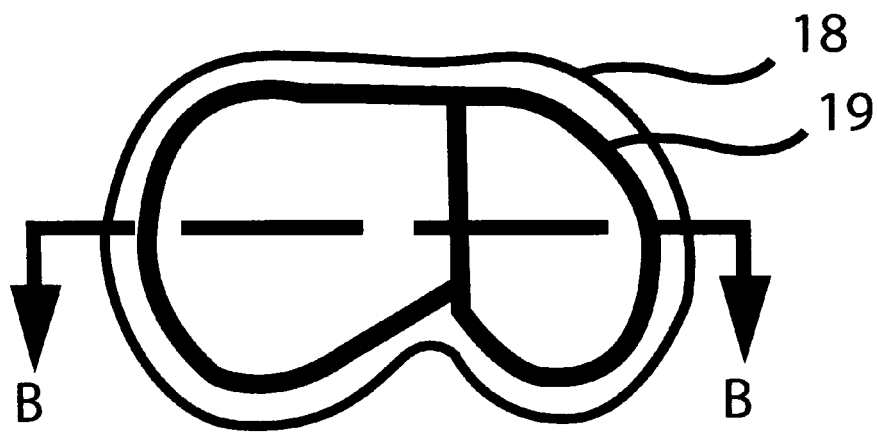
FIG. 32
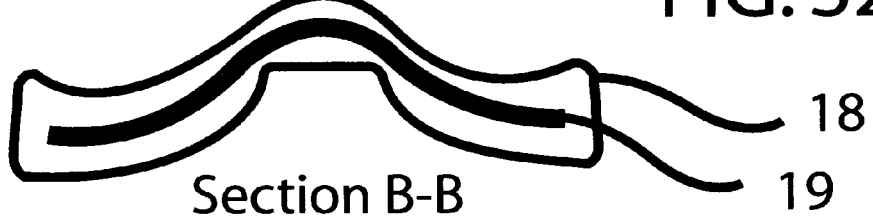
Section B-B
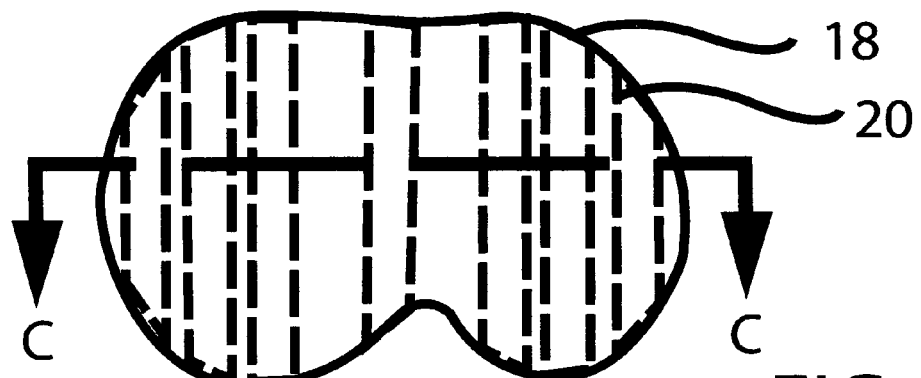
FIG. 33
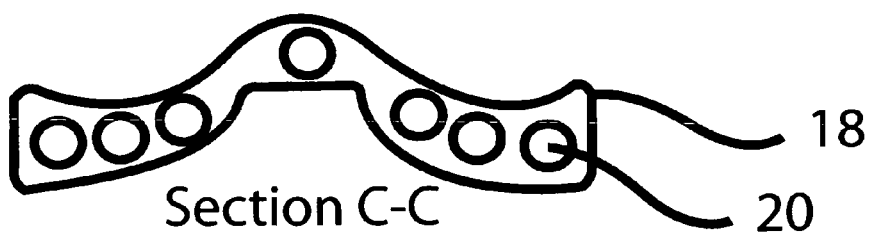
Section C-C

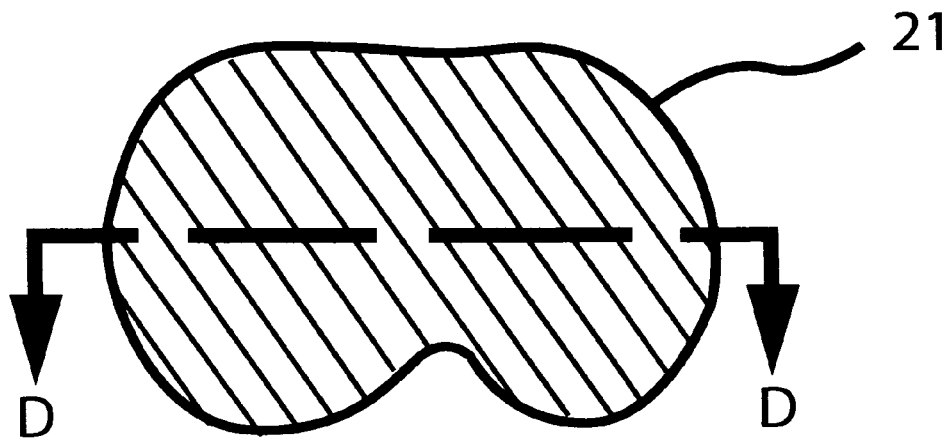
FIG. 34
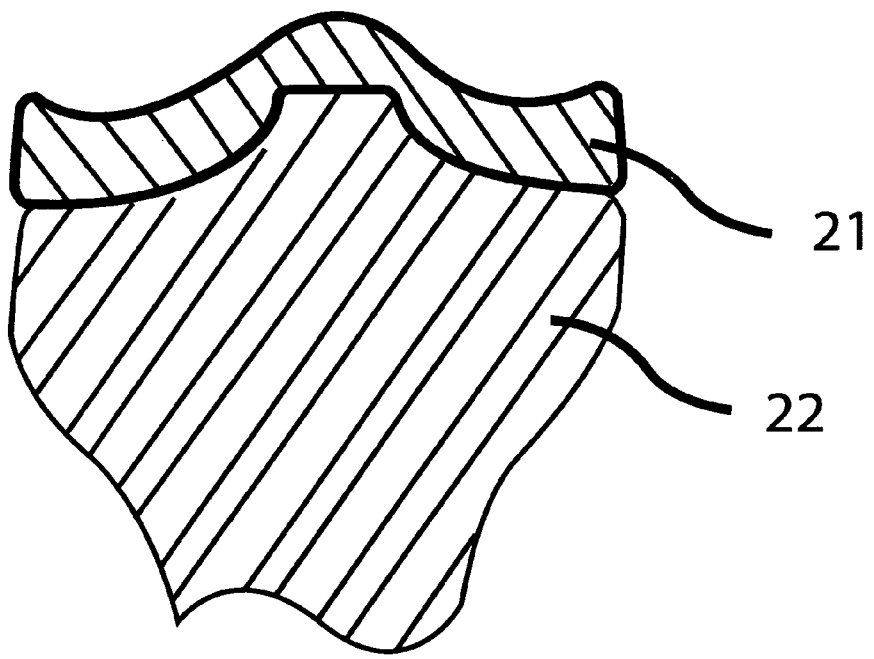
Section D-D

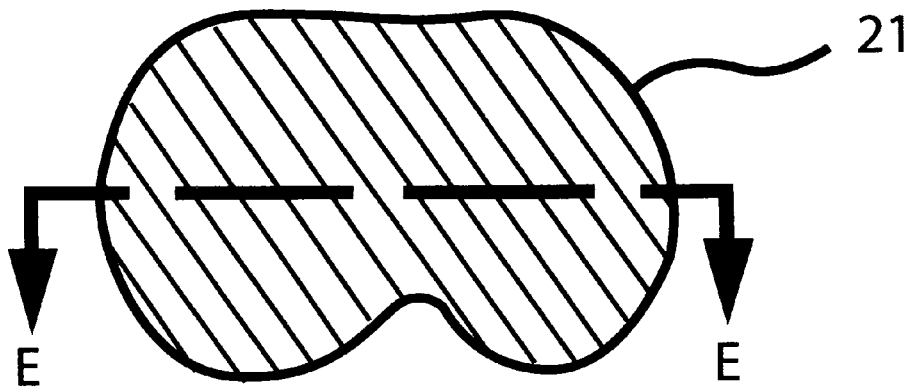
FIG. 38
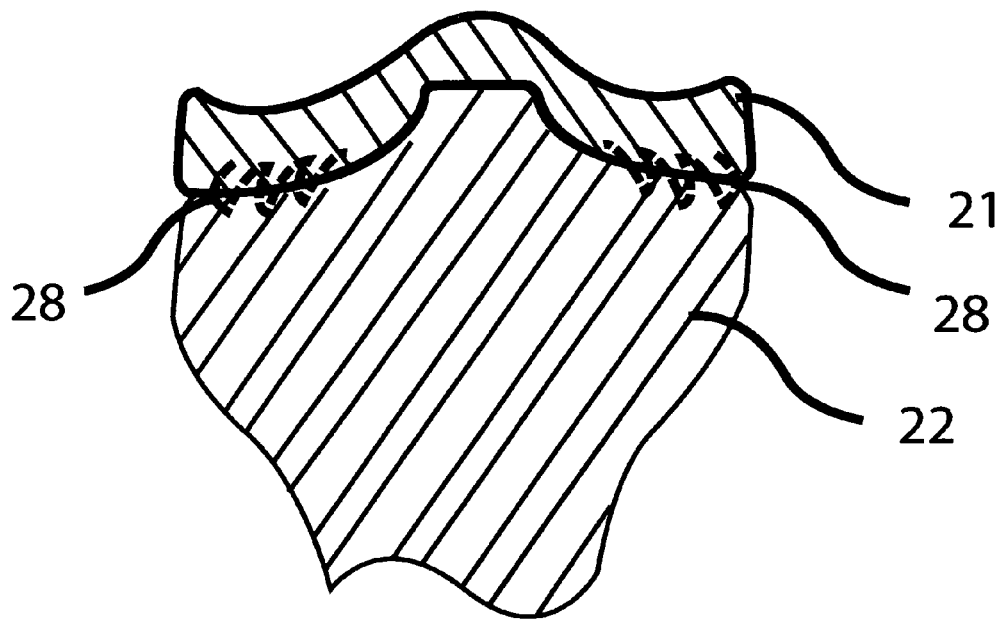
Section E-E

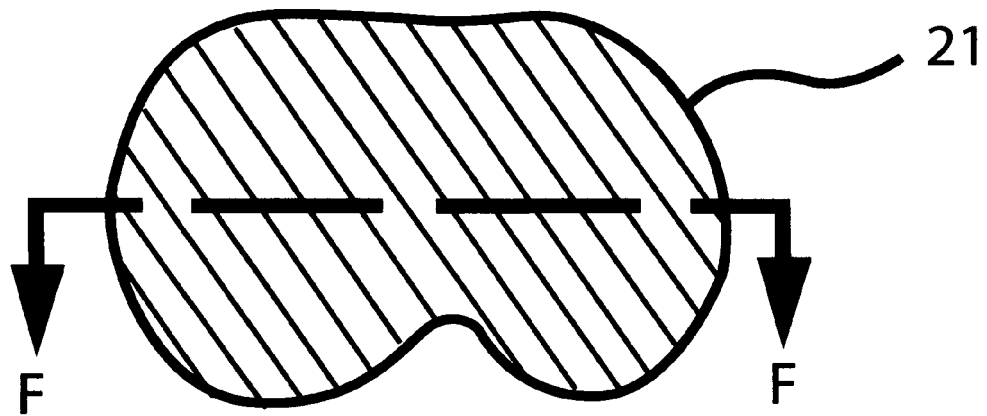
FIG. 39
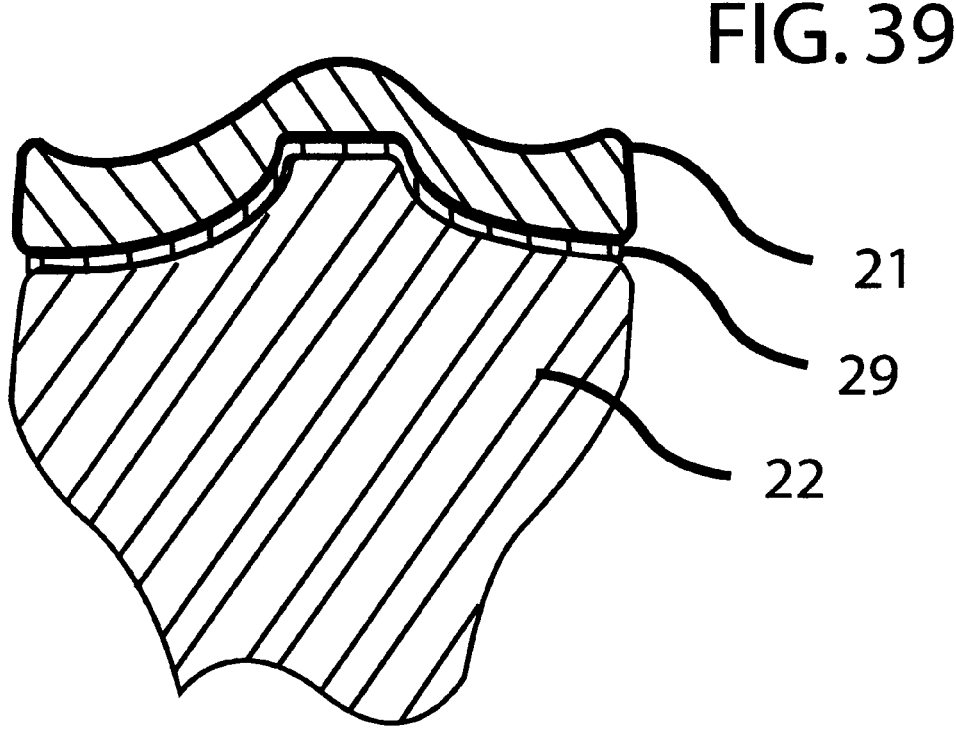
Section F-F

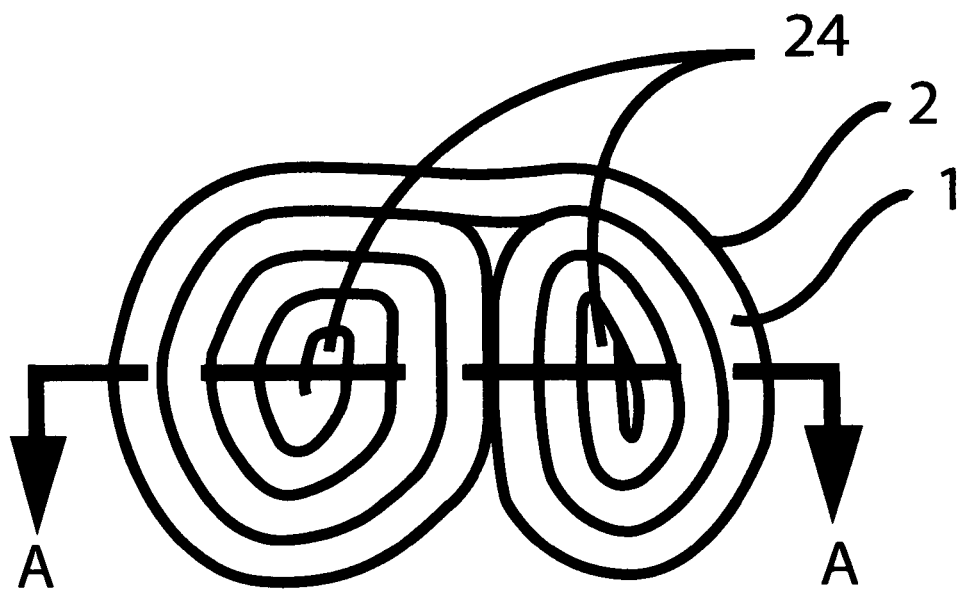
FIG. 40
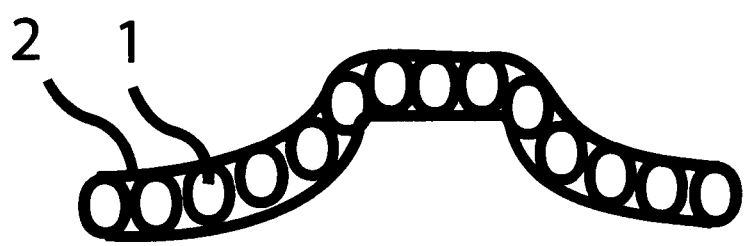
Section A-A

Section B-B

FLEXIBLY COMPLIANT CERAMIC PROSTHETIC MENISCUS FOR THE REPLACEMENT OF DAMAGED CARTILAGE IN ORTHOPEDIC SURGICAL REPAIR OR RECONSTRUCTION OF HIP, KNEE, ANKLE, SHOULDER, ELBOW, WRIST AND OTHER ANATOMICAL JOINTS

CROSS-REFERENCE TO RELATED APPLICATIONS

This Application claim priority to Provisional Application Ser. No. 61/130,279, filed on May 30, 2008 and Provisional Application Ser. No. 61/192,848, filed on Sep. 23, 2008.

RELATED U.S. PATENT DOCUMENTS

Federally Sponsored Research or Development

Not Applicable.

PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

This invention relates generally to surgical implants for the replacement of damaged or diseased cartilage in the surgical repair of a patient's articulating joint and the method of making such devices.

2. Description of Related Art

In the body, cartilage constitutes the lubricating wear surface, or meniscus, between bone ends in an anatomical joint. When the natural cartilage meniscus deteriorates or is damaged the orthopedic surgeon may replace the damaged or worn bone ends with metal prosthetic parts and insert an artificial meniscus, commonly made from ultra high molecular weight polyethylene to replace the worn out natural cartilage. This type of meniscus material has worked reasonably well. Newer ceramic prosthetic components have proved to be significantly superior because of their excellent wear characteristics. After initial failures, computer controlled machining technology has produced commercially successful spherically concentric ceramic hip and socket prosthetic components for total hip replacement surgeries. However, attempts at producing successful ceramic prosthetic components for knee, ankle, shoulder, elbow, wrist, and other joints have currently met with failure. The complex shapes of the bones within these joints, their rotation, and their movements have produced severe point-of-contact spike surface loadings resulting in broken or fractured ceramic prostheses which require surgical replacement. A new type of ceramic prosthetic meniscus construction is needed that is flexible and compliant to the surfaces of the bone ends within anatomical joints that are able to withstand these severe point-of-contact spike surface loadings in all the varied positions of the bones in those joints. A new type of ceramic prosthetic meniscus construction is needed that is applicable to all anatomical joints.

BRIEF SUMMARY OF THE INVENTION

The types of ceramic fiber prosthetic meniscus constructions described in this invention are applicable to the replacement of damaged cartilage in orthopedic surgical repair or reconstruction of hip, knee, ankle, shoulder, elbow, wrist, and other anatomical joints and provide the long wearing benefits of ceramics. They are inherently compliant to the surfaces of the bone ends of an anatomical joint eliminating the danger of severe point-of-contact spike surface loadings that are created in the many varied natural positions of the bones of a joint when an unexpected heavy joint loading occurs during a fall or under the other normal circumstances of life. They not only distribute both normal and extreme loads in a uniform manner onto the surfaces of the bone ends but they also are able to absorb and distribute body fluids to lubricate the joints to further extend the life of the joint. These types of ceramic fiber prosthetic meniscus constructions can be pre-bonded to prosthetic components in a variety of ways, as here in taught, prior to surgery so that they are ready to be installed in one piece at the time of surgery. Bone glue, which is in general use currently in orthopedic reconstructive surgery, would be a preferred choice to be used to cement these composite prostheses onto reconstructed bone ends. These types of ceramic fiber prosthetic meniscus constructions may also be able to be installed without surgical reconstruction of the bone ends under certain circumstances.

BRIEF DESCRIPTION OF THE SEVERAL VIEWS OF THE DRAWINGS

FIG. 1 shows the plan view and a sectional view of a ceramic fiber meniscus comprised of ceramic fibers formed into a rope-like construction which has been cut and coiled into a pad, with the cut ends placed into the interior of the pad.

FIG. 32 shows the plan view of the ceramic fiber meniscus of FIG. 3, or of FIG. 4, or of FIG. 5, or of FIG. 6, or of FIG. 8, or of FIG. 9, or of FIG. 10, or of FIG. 12, or of FIG. 13, or of FIG. 14, or of FIG. 16, or of FIG. 17, or of FIG. 18, or of FIG. 21, or of FIG. 22, or of FIG. 23, or of FIG. 24, or of FIG. 26, or of FIG. 27, or of FIG. 28, or of FIG. 29, which incorporates a metal perimeter wire to further restrict and control the lateral expansion of the flexibly compliant ceramic prosthetic meniscus.

FIG. 33 shows the plan view of the ceramic fiber meniscus of FIG. 4, or of FIG. 5, or of FIG. 6, or of FIG. 8, or of FIG. 9, or of FIG. 10, or of FIG. 12, or of FIG. 13, or of FIG. 14, or of FIG. 16, or of FIG. 17, or of FIG. 18, or of FIG. 21, or of FIG. 22, or of FIG. 23, or of FIG. 24, or of FIG. 26, or of FIG. 27, or of FIG. 28, or of FIG. 29, which incorporates voids to increase the compliant flexibility of the flexibly compliant ceramic prosthetic meniscus.

FIG. 34 shows the plan view and a sectional view of a ceramic fiber meniscus attached to a bone end.

FIG. 38 shows the plan view of the ceramic fiber meniscus of FIG. 35 thermally bonded onto a metal prosthesis by means of sewing.

FIG. 39 shows the plan view and a sectional view of a ceramic fiber meniscus of FIG. 35 attached to a bone end by allowing the remaining cartilage tissue to grow onto the ceramic meniscus.

FIG. 40 shows a plan view and a sectional view of an implantable ceramic fiber meniscus pad.

DETAILED DESCRIPTION OF THE INVENTION

The flexibly compliant ceramic fiber prosthetic meniscus construction described in this invention is somewhat compressible and is continuously flexible so as to fit and match the surfaces of the bone ends of an articulating anatomical joint so as to evenly distribute body loads onto the bones of that joint regardless of the positions of the bone ends within that joint. This evenly distributed loading eliminates severe point-of-contact-surface-loads which may be caused by a fall, an accident, or by other means, which can fracture or otherwise damage solid ceramic surfaced prosthetic components which must then be surgically replaced. This ceramic fiber prosthetic meniscus construction provides the desirable long wearing characteristics of ceramics and also absorbs and distributes body fluids to lubricate and further extend the life of the joint. Deterioration of the bone tissue caused by the presence of polyethylene "macrophages" is no longer an issue since no polyethylene is present. For purposes of teaching this invention all of the embodiments described and illustrated here in relate to the knee joint.

FIG. 1 shows the plan view and sectional view of a flexibly compliant ceramic prosthetic meniscus [1] for the repair or replacement of damaged cartilage in the orthopedic surgical repair or reconstruction of hip, knee, ankle, shoulder, elbow, wrist, and other anatomical joints, comprised of ceramic fibers [2] which have been formed together into a rope-like construction which has been cut and coiled into a pad with the cut ends placed into the interior of the pad.

Figure 2:
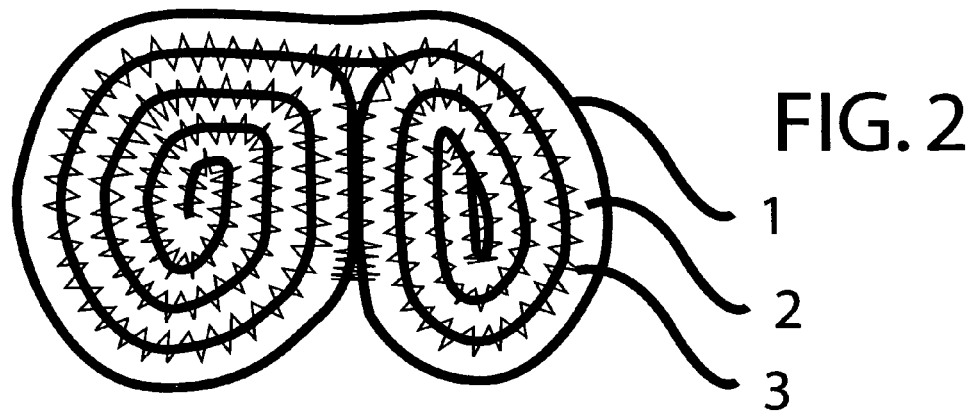
FIG. 2 shows the plan view of the ceramic fiber meniscus of FIG. 1 which is sewn together with a zigzag stitch pattern.

FIG. 2 shows the plan view of the flexibly compliant ceramic prosthetic meniscus [1] of FIG. 1 comprised of ceramic fibers [2] which have been formed together into a rope-like construction which has been cut and coiled into a pad, with the cut ends placed into the interior of the pad, which pad has been sewn together with a zigzag stitch pattern [3] to join the adjacent ceramic fiber rope-like coils of the pad.

Figure 3:
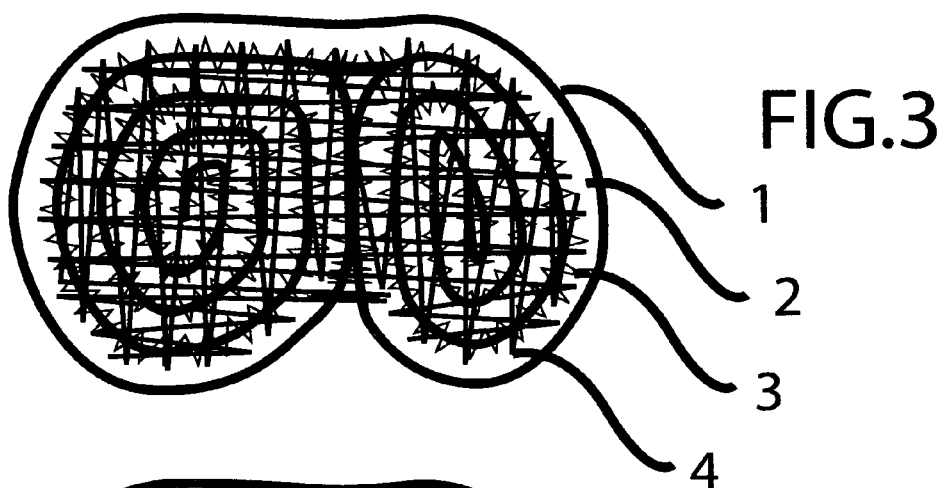
FIG. 3 shows the plan view of the ceramic fiber meniscus of FIG. 2 which is over-sewn with multiple vertical and horizontal rows of stitches.

FIG. 3 shows the plan view of a flexibly compliant ceramic prosthetic meniscus [1] of FIG. 1 comprised of ceramic fibers

[2] which have been formed together into a rope-like construction which has been cut and coiled into a pad with the cut ends placed into the interior of the pad, which pad has been sewn together with a zigzag stitch pattern [3] to join the adjacent ceramic fiber rope-like coils of the pad, and which pad has been thereafter over-sewn with multiple vertical and horizontal rows of stitches [3] so as to create an integral, dimensionally stable, and flexibly compliant ceramic prosthetic meniscus.

Figure 4:
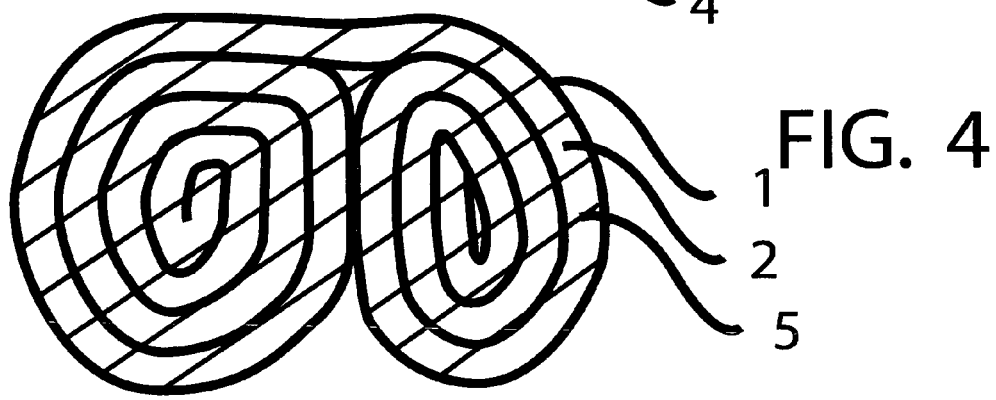
FIG. 4 shows the plan view of the ceramic fiber meniscus of FIG. 1 fixed together by being thermally fused.

FIG. 4 shows the plan view of a flexibly compliant ceramic prosthetic meniscus [1] of FIG. 1 comprised of ceramic fibers [2] which have been formed together into a rope-like construction which has been cut and coiled into a pad with the cut ends placed into the interior of the pad [1], which pad has been thermally fused [5] so as to create an integral, dimensionally stable, and flexibly compliant ceramic prosthetic meniscus.

Figure 5:
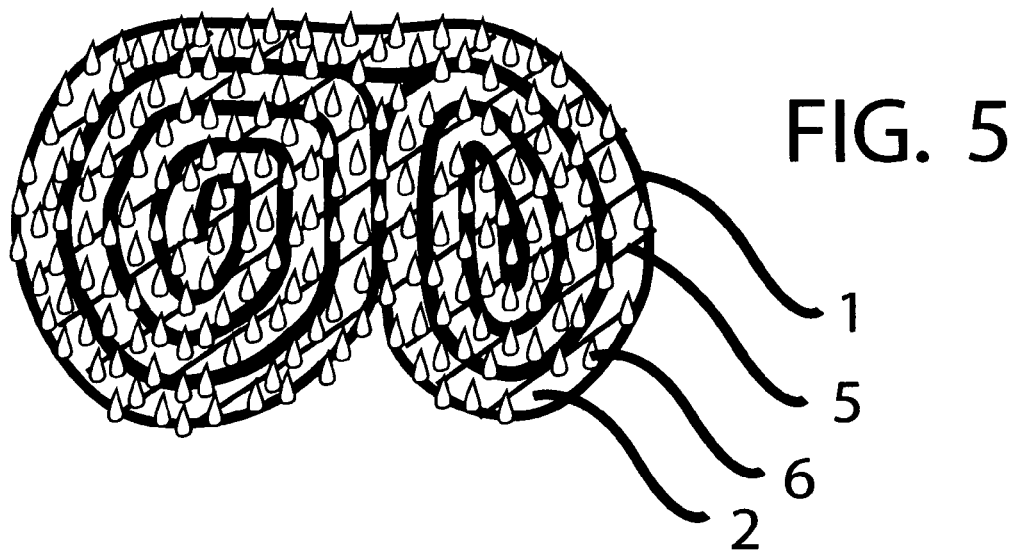
FIG. 5 shows the plan view of the ceramic fiber meniscus of FIG. 1 being wetted with a liquid ceramic material and being fixed together by being thermally fused.

FIG. 5 shows the plan view of a flexibly compliant ceramic prosthetic meniscus [1] of FIG. 1 comprised of ceramic fibers [2] which have been formed together into a rope-like construction which has been cut and coiled into a pad with the cut ends placed into the interior of the pad, which pad has been wetted with a liquid ceramic material [6] which has a significantly lower melting temperature than that of the ceramic fibers, and which wetted pad has been thermally fused [5] so as to create an integral, dimensionally stable, and flexibly compliant ceramic prosthetic meniscus.

Figure 6:
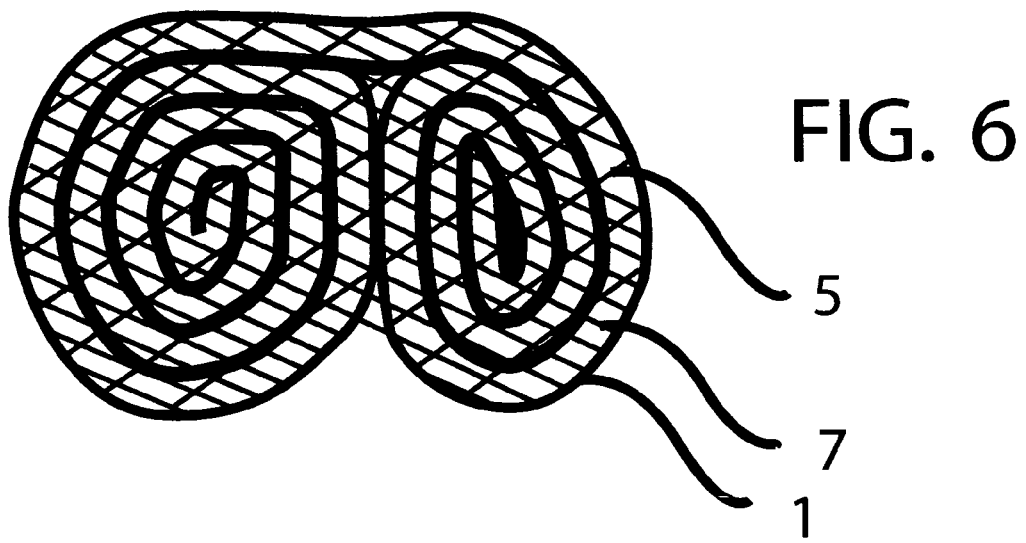
FIG. 6 shows the plan view of the ceramic fiber meniscus of FIG. 1, comprised of ceramic fibers having two significantly different melting temperatures, fixed together by being thermally fused.

FIG. 6 shows the plan view of a flexibly compliant ceramic prosthetic meniscus [1] of FIG. 1 comprised of ceramic fibers which have two significantly different melting temperatures [7], which have been formed together into a rope-like construction which has been cut and coiled into a pad with the cut ends placed into the interior of the pad, which pad has been thermally fused [5] so as to create an integral, dimensionally stable, and flexibly compliant ceramic prosthetic meniscus.

Figure 7:
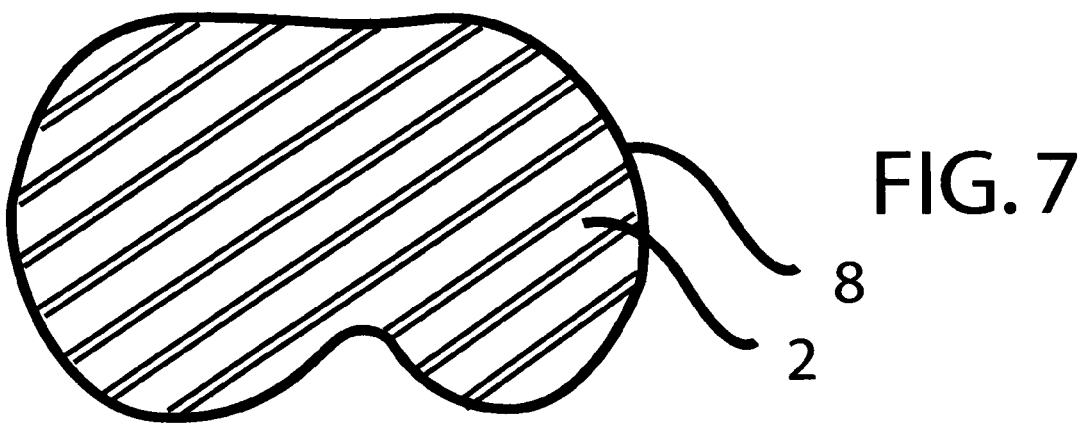
FIG. 7 shows the plan view of a ceramic fiber meniscus comprised of ceramic fibers fixed together into a non-woven felt-like pad.

FIG. 7 shows the plan view of a flexibly compliant ceramic prosthetic meniscus [8] for the repair or replacement of damaged cartilage in the orthopedic surgical repair or reconstruction of hip, knee, ankle, shoulder, elbow, wrist, and other anatomical joints comprised of ceramic fibers [2] fixed together into a non-woven felt-like pad so as to create an integral, dimensionally stable, and flexibly compliant ceramic prosthetic meniscus.

Figure 8:
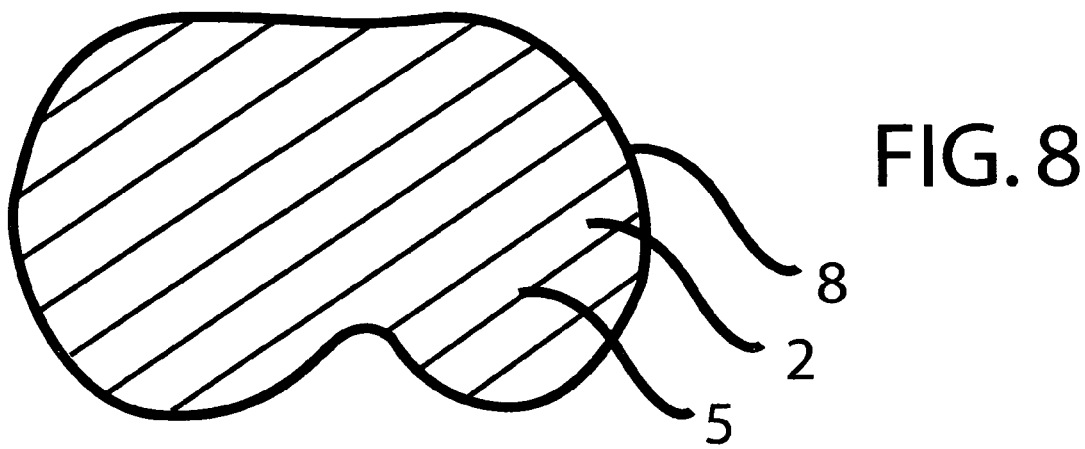
FIG. 8 shows the plan view of the ceramic fiber meniscus of FIG. 7 fixed together by being thermally fused.

FIG. 8 shows the plan view of the meniscus [8] of FIG. 7, comprised of ceramic fibers [2], which has been thermally fused together [5] so as to create an integral, dimensionally stable, and flexibly compliant ceramic prosthetic meniscus.

Figure 9:
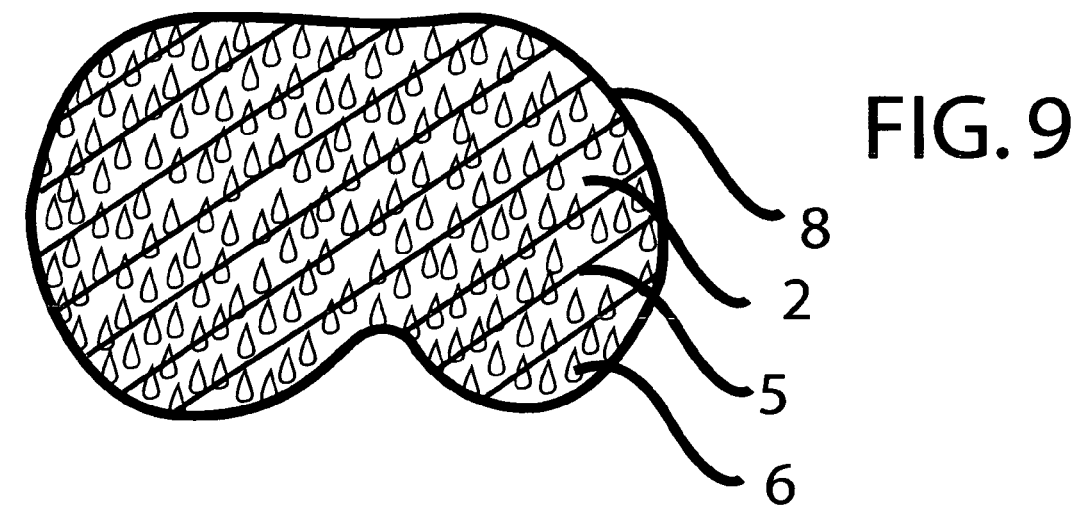
FIG. 9 shows the plan view of the ceramic fiber meniscus of FIG. 8 being wetted with a liquid ceramic material and fixed together by being thermally fused.

FIG. 9 shows the plan view of the meniscus [8] of FIG. 7 comprised of ceramic fibers [2] which have been wetted with a liquid ceramic material [6] which has a significantly lower melting temperature than that of the ceramic fibers, and which wetted pad has been thermally fused [5] so as to create an integral,
dimensionally stable, and flexibly compliant ceramic prosthetic meniscus.

Figure 10:
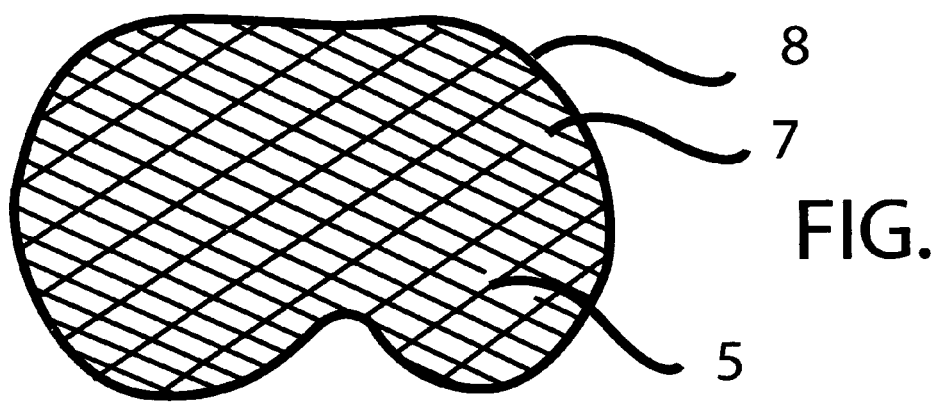
FIG. 10 shows the plan view of the ceramic fiber meniscus of FIG. 8 comprised of ceramic fibers having two different melting temperatures and fixed together by being thermally fused.

FIG. 10 shows the plan view of the meniscus [8] of FIG. 7 comprised of ceramic fibers having two different melting temperatures [7], which meniscus has been thermally fused [5] so as to create an integral, dimensionally stable, and flexibly compliant ceramic prosthetic meniscus.

Figure 11:
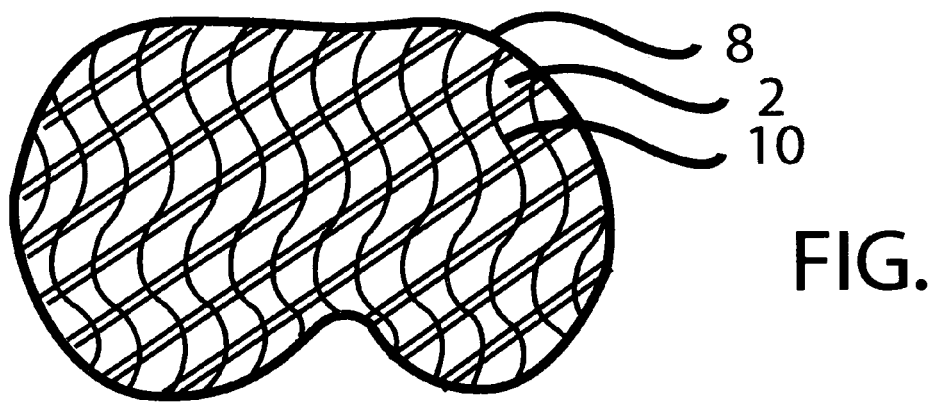
FIG. 11 shows the plan view of the ceramic fiber meniscus of FIG. 7 comprised of ceramic fibers and polyethylene fibers fixed together in a non-woven felt-like pad.

FIG. 11 shows the plan view of the meniscus [8] of FIG. 7 comprised of ceramic fibers [2] and polyethylene fibers [10], which have been fixed together fixed together into a non-woven felt-like pad so as to create an integral, dimensionally stable, and flexibly compliant ceramic prosthetic meniscus.

Figure 12:
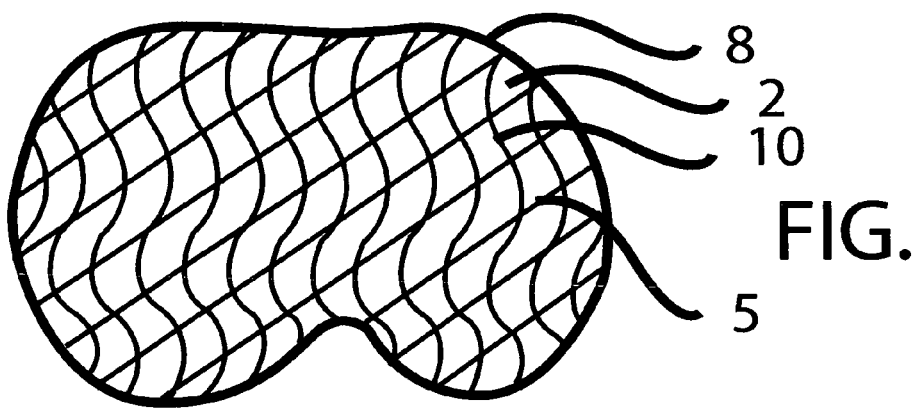
FIG. 12 shows the plan view of the ceramic fiber meniscus of FIG. 11 fixed together by being thermally fused.

FIG. 12 shows the plan view of the meniscus [8] of FIG. 11 comprised of ceramic fibers [2] and polyethylene fibers [10], which have been thermally fused [5] so as to create an integral, dimensionally stable, and flexibly compliant ceramic prosthetic meniscus.

Figure 13:
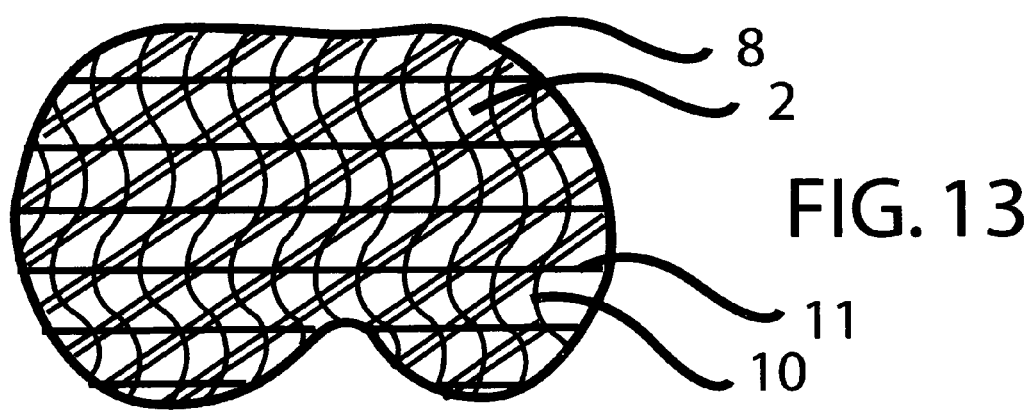
FIG. 13 shows the plan view of the ceramic fiber meniscus of FIG. 11 fixed together by compression molding.

FIG. 13 shows the plan view of the meniscus [8] of FIG. 11 comprised of ceramic fibers [2] and polyethylene fibers [10], which have been fixed together by compression molding [11] so as to create an integral, dimensionally stable, and flexibly compliant ceramic prosthetic meniscus.

Figure 14:
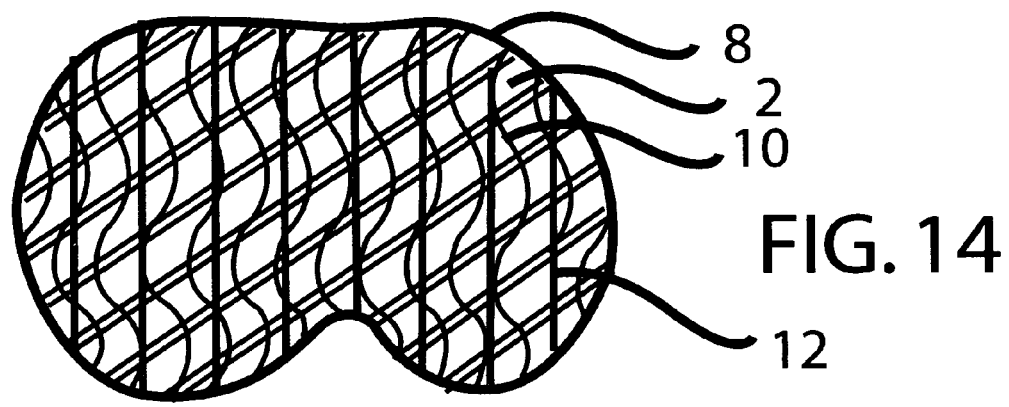
FIG. 14 shows the plan view of the ceramic fiber meniscus of FIG. 11 fixed together by injection molding.

FIG. 14 shows the plan view of the meniscus [8] of FIG. 11 comprised of ceramic fibers [2] and polyethylene fibers [10], which have been fixed together by injection molding [12] so as to create an integral, dimensionally stable, and flexibly compliant ceramic prosthetic meniscus.

Figure 15:
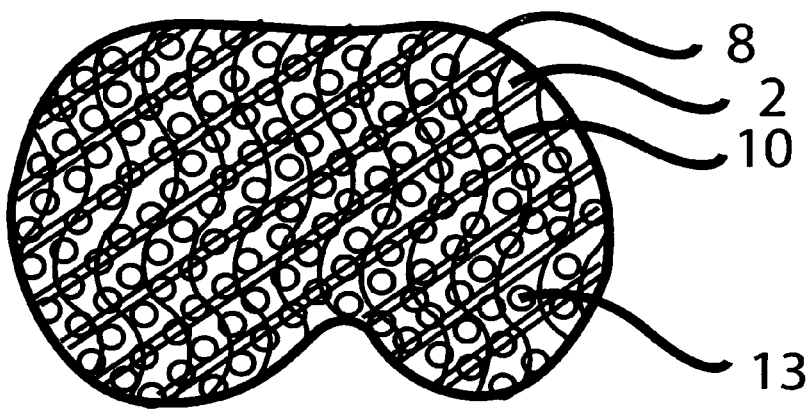
FIG. 15 shows the plan view of the ceramic fiber meniscus of FIG. 7 comprised of ceramic fibers, polyethylene fibers, and ceramic beads fixed together in a non-woven felt-like pad.

FIG. 15 shows the plan view of the meniscus [8] of FIG. 7 comprised of ceramic fibers [2], polyethylene fibers [10], and ceramic beads [13] fixed together into a non-woven felt-like pad so as to create an integral, dimensionally stable, and flexibly compliant ceramic prosthetic meniscus.

Figure 16:
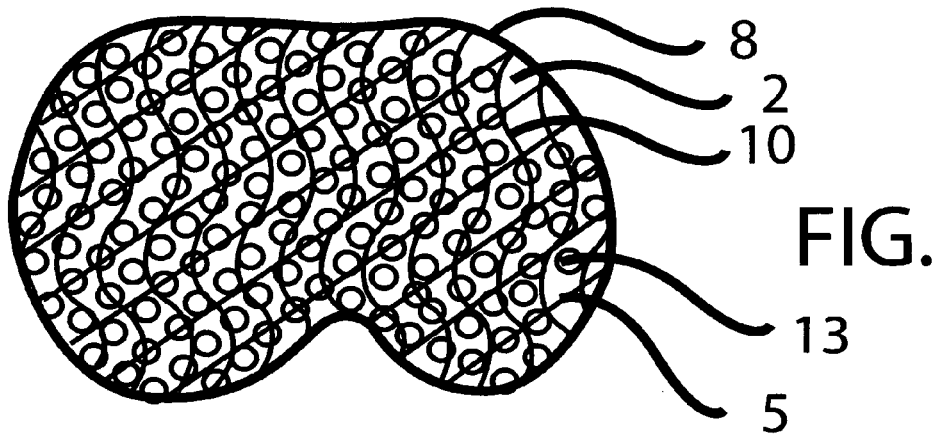
FIG. 16 shows the plan view of the ceramic fiber meniscus of FIG. 15 fixed together by being thermally fused.

FIG. 16 shows the plan view of the meniscus [8] of FIG. 11 comprised of ceramic fibers [2], polyethylene fibers [10], and ceramic beads [13] which have been thermally fused [5] so as to create an integral, dimensionally stable, and flexibly compliant ceramic prosthetic meniscus.

Figure 17:
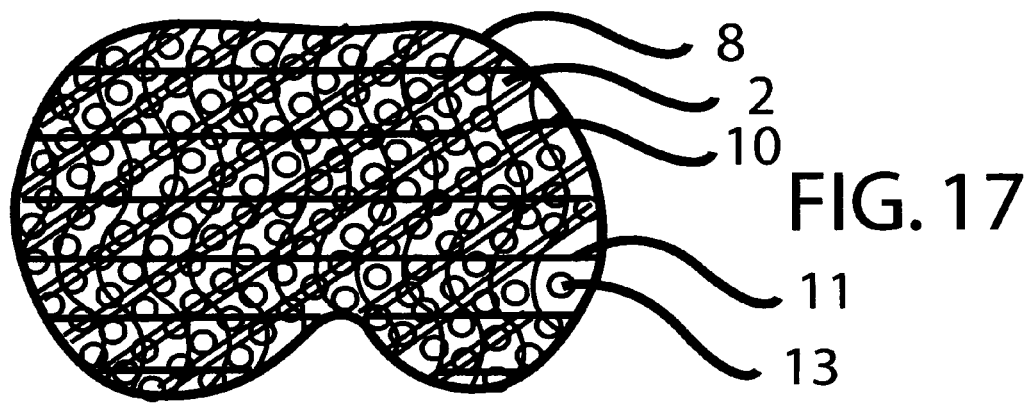
FIG. 17 shows the plan view of the ceramic fiber meniscus of FIG. 16 fixed together by compression molding.

FIG. 17 shows the plan view of the meniscus [8] of FIG. 11 comprised of ceramic fibers [2], polyethylene fibers [10], and ceramic beads [13] which have been fixed together by compression molding [11] so as to create an integral, dimensionally stable, and flexibly compliant ceramic prosthetic meniscus.

Figure 18:
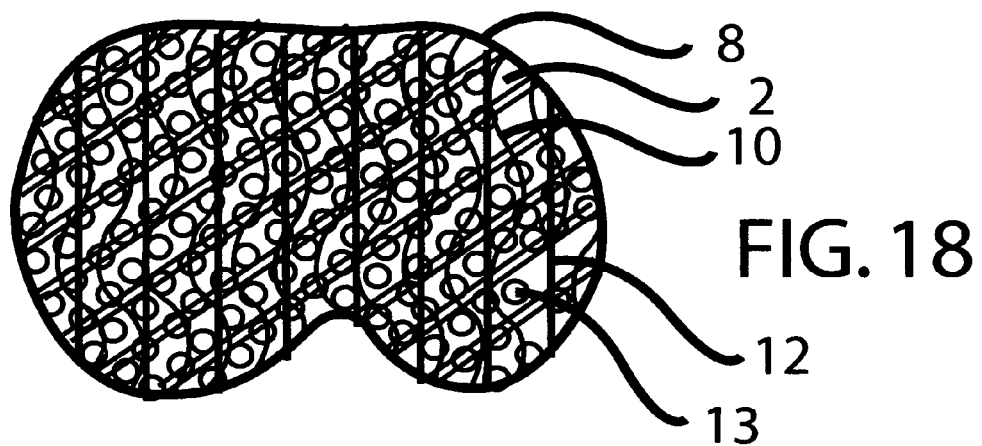
FIG. 18 shows the plan view of the ceramic fiber meniscus of FIG. 16 fixed together by injection molding.

FIG. 18 shows the plan view of the meniscus [8] of FIG. 11 comprised of ceramic fibers [2], polyethylene fibers [10], and ceramic beads [13] which have been fixed together by injection molding [12] so as to create an integral, dimensionally stable, and flexibly compliant ceramic prosthetic meniscus.

Figure 19:
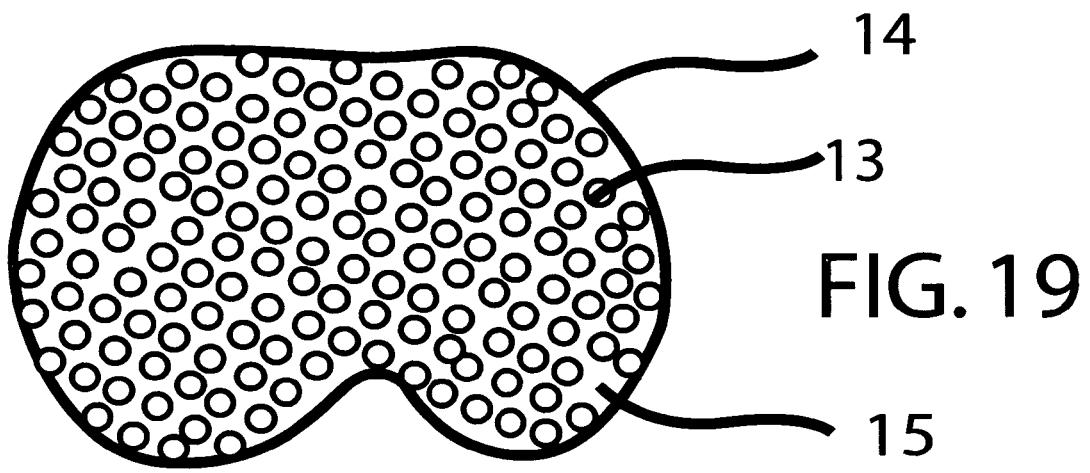
FIG. 19 shows the plan view of a ceramic meniscus comprised of ceramic beads fixed together in a matrix of polyethylene.

FIG. 19. shows the plan view of a flexibly compliant ceramic prosthetic meniscus [14] comprised of ceramic beads [13] imbedded in a matrix of polyethylene [15] so as to create an integral, dimensionally stable, and flexibly compliant ceramic prosthetic meniscus.

Figure 20:
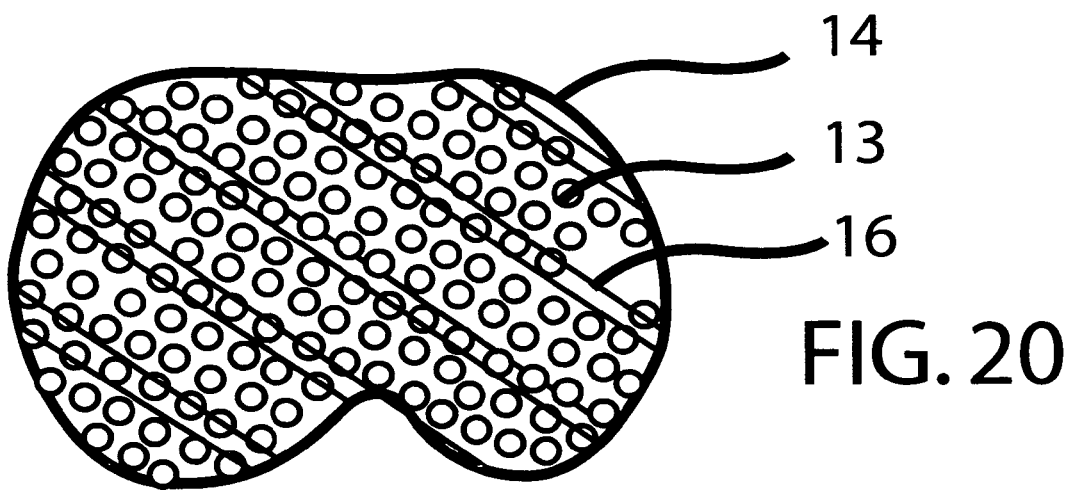
FIG. 20 shows the plan view of the ceramic meniscus of FIG. 19 fixed together by being imbedded in a matrix of solid polyethylene.

FIG. 20. shows the plan view of a flexibly compliant ceramic prosthetic meniscus [14] comprised of ceramic beads [13] imbedded in a matrix of solid polyethylene [16] so as to create an integral, dimensionally stable, and flexibly compliant ceramic prosthetic meniscus.

Figure 21:
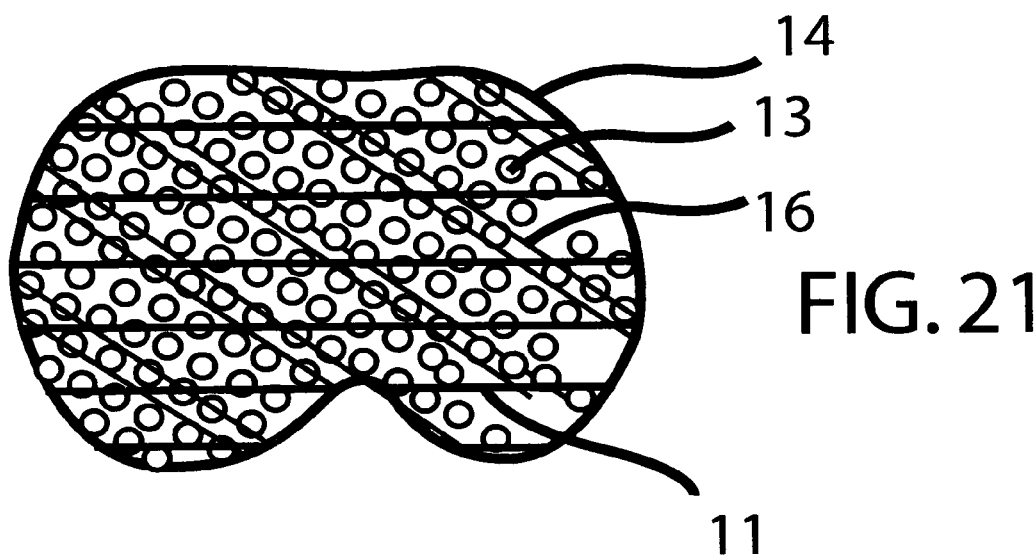
FIG. 21 shows the plan view of the ceramic meniscus of FIG. 20 fixed together by compression molding.

FIG. 21. shows the plan view of a flexibly compliant ceramic prosthetic meniscus [14] comprised of ceramic beads [13] imbedded in a matrix of solid polyethylene [16] which have been fixed together by compression molding [11] so as to create an integral, dimensionally stable, and flexibly compliant ceramic prosthetic meniscus.

Figure 22:
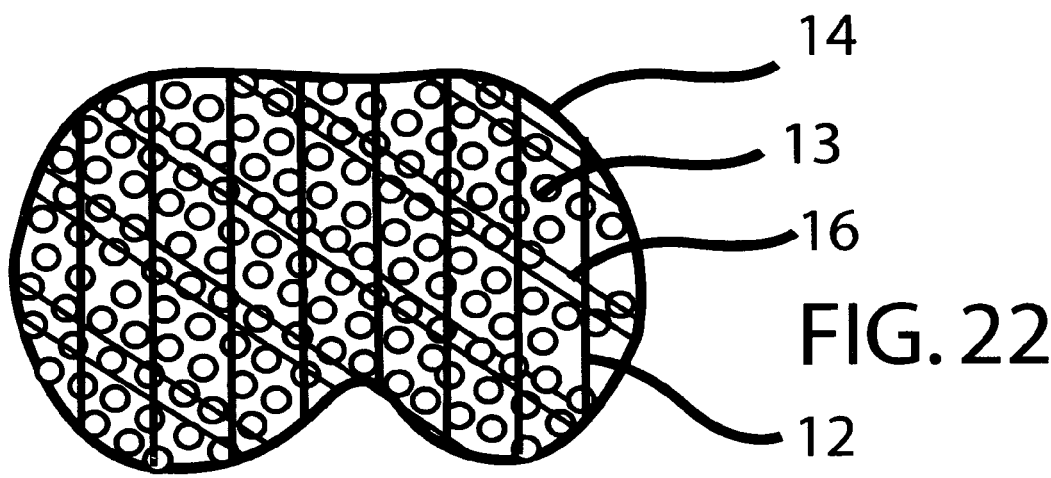
FIG. 22 shows the plan view of the ceramic meniscus of FIG. 20 fixed together by injection molding.

FIG. 22. shows the plan view of a flexibly compliant ceramic prosthetic meniscus [14] comprised of ceramic beads [13] imbedded in a matrix of solid polyethylene [16] which have been fixed together by injection molding [12] so as to create an integral, dimensionally stable, and flexibly compliant ceramic prosthetic meniscus.

Figure 23:
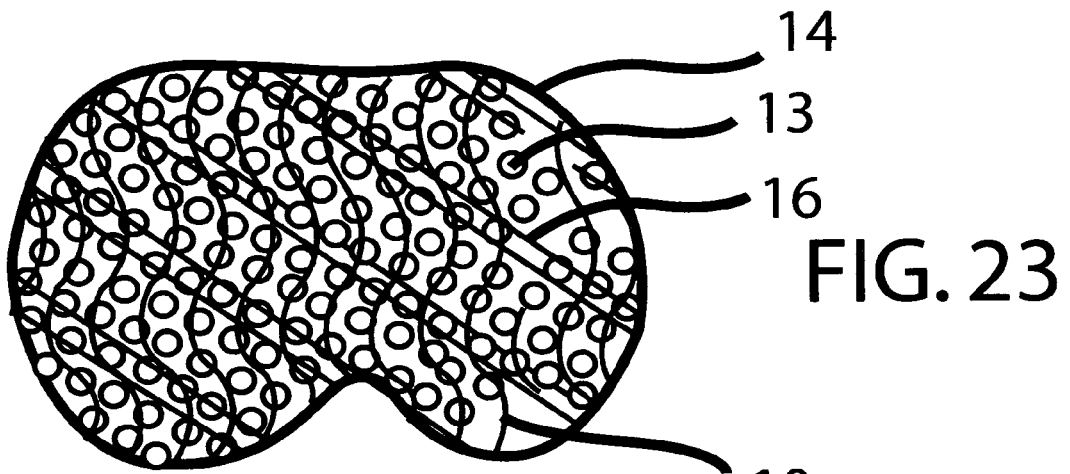
FIG. 23 shows the plan view of the ceramic fiber meniscus of FIG. 20 comprised of ceramic beads and ceramic fibers.

FIG. 23. shows the plan view of a flexibly compliant ceramic prosthetic meniscus [14] comprised of ceramic beads [13] and ceramic fibers [10] imbedded in a matrix of solid polyethylene [16] which have been fixed together so as to create an integral, dimensionally stable, and flexibly compliant ceramic prosthetic meniscus.

Figure 24:
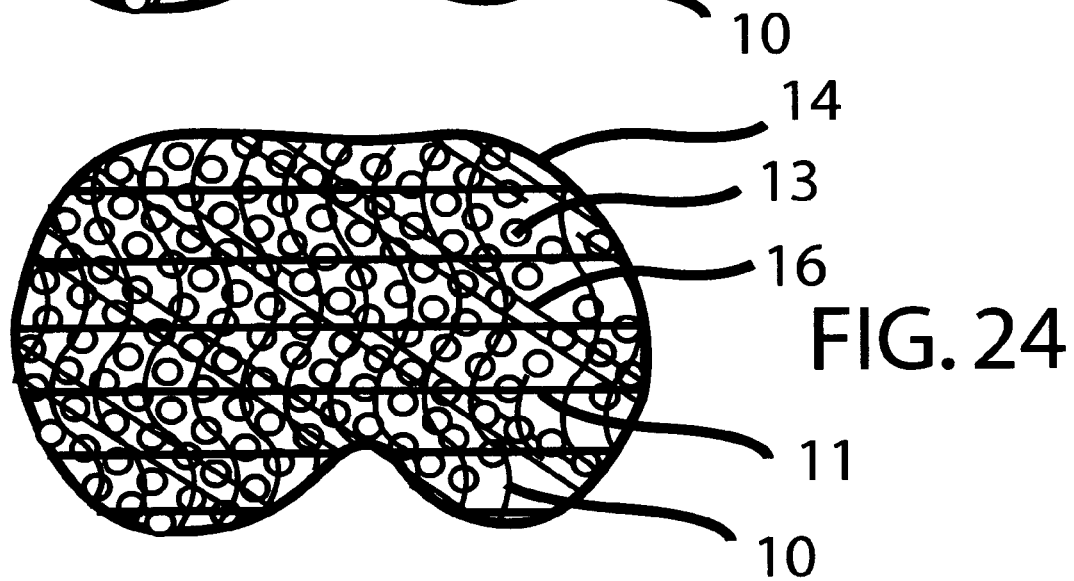
FIG. 24 shows the plan view of the ceramic fiber meniscus of FIG. 23 fixed together by compression molding.

FIG. 24. shows the plan view of a flexibly compliant ceramic prosthetic meniscus [14] comprised of ceramic beads [13] and ceramic fibers [10] imbedded in a matrix of solid polyethylene [16] which have been fixed together by compression molding [11] so as to create an integral, dimensionally stable, and flexibly compliant ceramic prosthetic meniscus.

Figure 25:
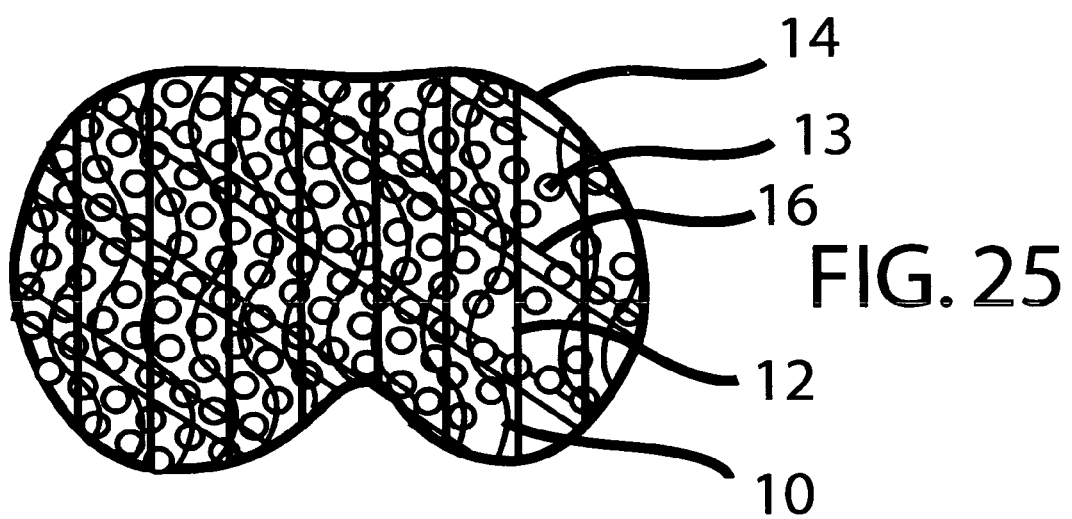
FIG. 25 shows the plan view of the ceramic fiber meniscus of FIG. 23 fixed together by injection molding.

FIG. 25. shows the plan view of a flexibly compliant ceramic prosthetic meniscus [14] comprised of ceramic beads [13] and ceramic fibers [10] imbedded in a matrix of solid polyethylene [16] which have been fixed together by injection molding [12] so as to create an integral, dimensionally stable, and flexibly compliant ceramic prosthetic meniscus.

Figure 26:
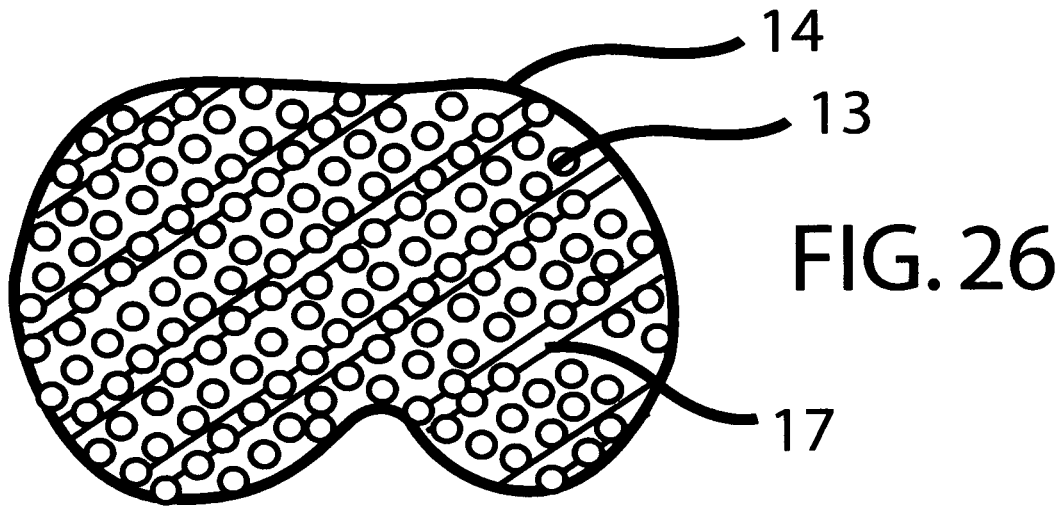
FIG. 26 shows the plan view of the ceramic fiber meniscus of FIG. 19 comprised of ceramic beads fixed together in a matrix of structural foam polyethylene.

FIG. 26. shows the plan view of a flexibly compliant ceramic prosthetic meniscus [14] comprised of ceramic beads [13] imbedded in a matrix of structural foam polyethylene [17] so as to create an integral, dimensionally stable, and flexibly compliant ceramic prosthetic meniscus.

Figure 27:
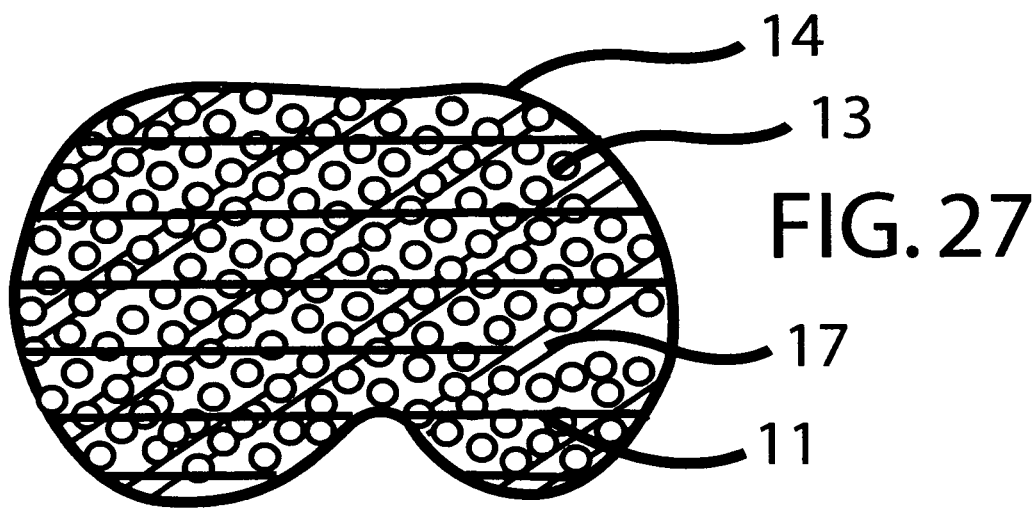
FIG. 27 shows the plan view of the ceramic fiber meniscus of FIG. 26 fixed together by compression molding.

FIG. 27. shows the plan view of a flexibly compliant ceramic prosthetic meniscus [14] comprised of ceramic beads [13] imbedded in a matrix of structural foam polyethylene [17] which have been fixed together by compression molding [11] so as to create an integral, dimensionally stable, and flexibly compliant ceramic prosthetic meniscus.

Figure 28:
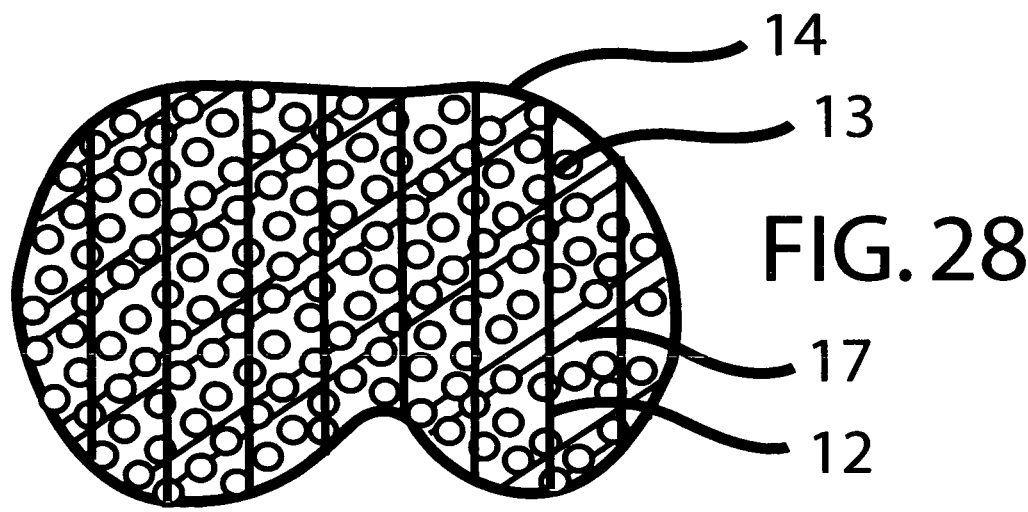
FIG. 28 shows the plan view of the ceramic fiber meniscus of FIG. 26 fixed together by injection molding.

FIG. 28. shows the plan view of a flexibly compliant ceramic prosthetic meniscus [14] comprised of ceramic beads [13] imbedded in a matrix of structural foam polyethylene [17] which have been fixed together by injection molding [12] so as to create an integral, dimensionally stable, and flexibly compliant ceramic prosthetic meniscus.

Figure 29:
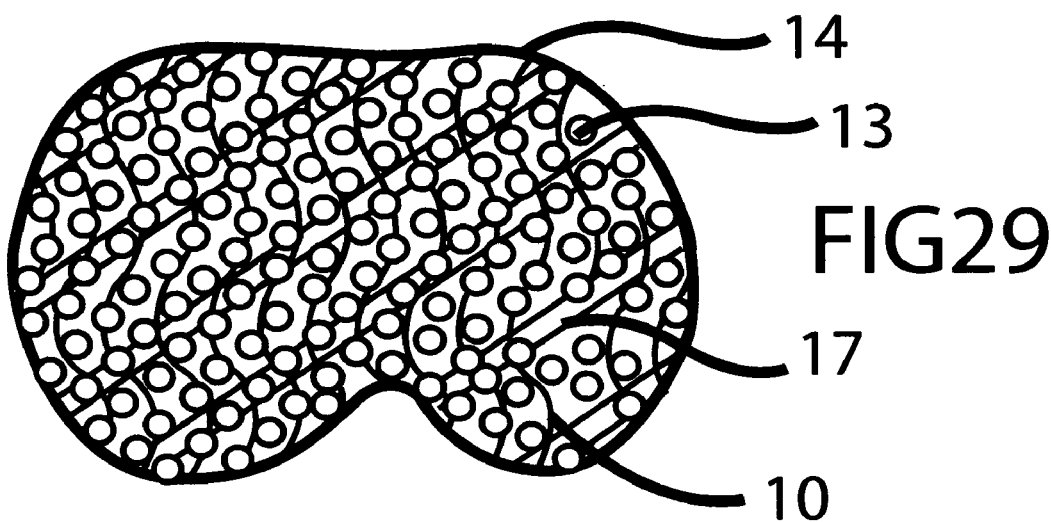
FIG. 29 shows the plan view of the ceramic fiber meniscus of FIG. 23 comprised of ceramic beads and ceramic fibers fixed together in a matrix of structural foam polyethylene.

FIG. 29. shows the plan view of a flexibly compliant ceramic prosthetic meniscus [14] comprised of ceramic beads [13] and ceramic fibers [10] imbedded in a matrix of structural foam polyethylene [17] which have been fixed together by compression molding [11] so as to create an integral, dimensionally stable, and flexibly compliant ceramic prosthetic meniscus.

Figure 30:
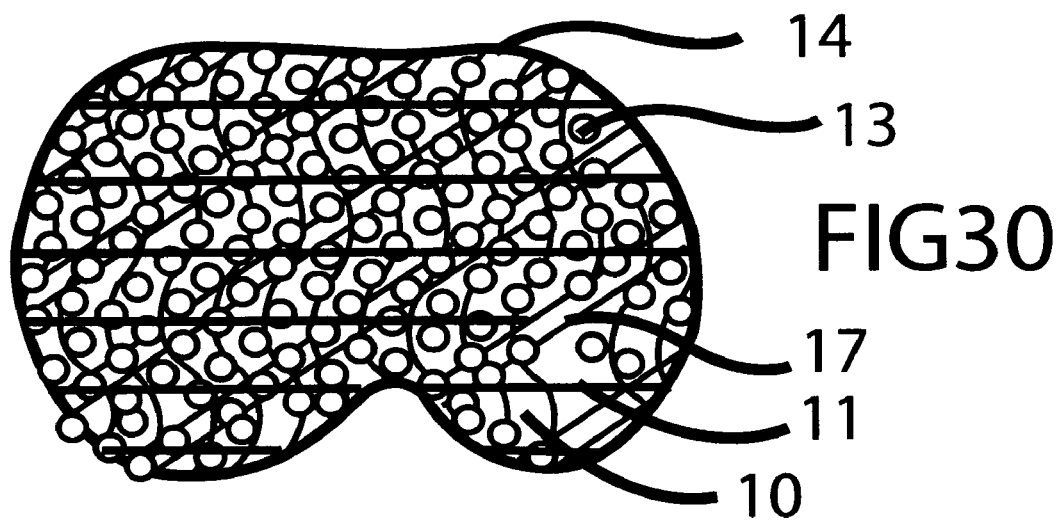
FIG. 30 shows the plan view of the ceramic fiber meniscus of FIG. 26 fixed together by compression molding.

FIG. 30. shows the plan view of a flexibly compliant ceramic prosthetic meniscus [14] comprised of ceramic beads [13] and ceramic fibers [10] imbedded in a matrix of structural foam polyethylene [17] which have been fixed together by compression molding [11] so as to create an integral, dimensionally stable, and flexibly compliant ceramic prosthetic meniscus.

Figure 31:
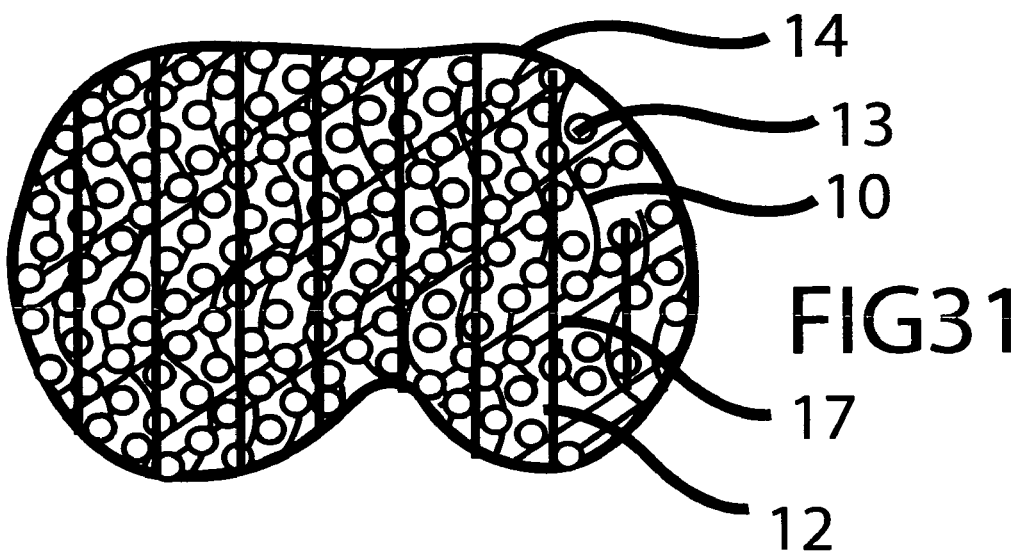
FIG. 31 shows the plan view of the ceramic fiber meniscus of FIG. 26 fixed together by injection molding.

FIG. 31. shows the plan view of a flexibly compliant ceramic prosthetic meniscus [14] comprised of ceramic beads [13] and ceramic fibers [10] imbedded in a matrix of structural foam polyethylene [17] which have been fixed together by injection molding [12] so as to create an integral, dimensionally stable, and flexibly compliant ceramic prosthetic meniscus.

FIG. 32 shows the plan view of the ceramic fiber meniscus [18] of FIG. 3, or of FIG. 4, or of FIG. 5, or of FIG. 6, or of FIG. 8, or of FIG. 9, or of FIG. 10, or of FIG. 12, or of FIG. 13, or of FIG. 14, or of FIG. 16, or of FIG. 17, or of FIG. 18, or of FIG. 21, or of FIG. 22, or of FIG. 23, or of FIG. 24, or of FIG. 26, or of FIG. 27, or of FIG. 28, or of FIG. 29, which incorporates a metal perimeter wire [19] to further restrict and control the lateral expansion of the flexibly compliant ceramic prosthetic meniscus.

FIG. 33 shows the plan view of the ceramic fiber meniscus [19] of FIG. 4, or of FIG. 5, or of FIG. 6, or of FIG. 8, or of FIG. 9, or of FIG. 10, or of FIG. 12, or of FIG. 13, or of FIG. 14, or of FIG. 16, or of FIG. 17, or of FIG. 18, or of FIG. 21, or of FIG. 22, or of FIG. 23, or of FIG. 24, or of FIG. 26, or of FIG. 27, or of FIG. 28, or of FIG. 29, which incorporates voids [20] to increase the compliant flexibility of the flexibly compliant ceramic prosthetic meniscus.

Figure 35:
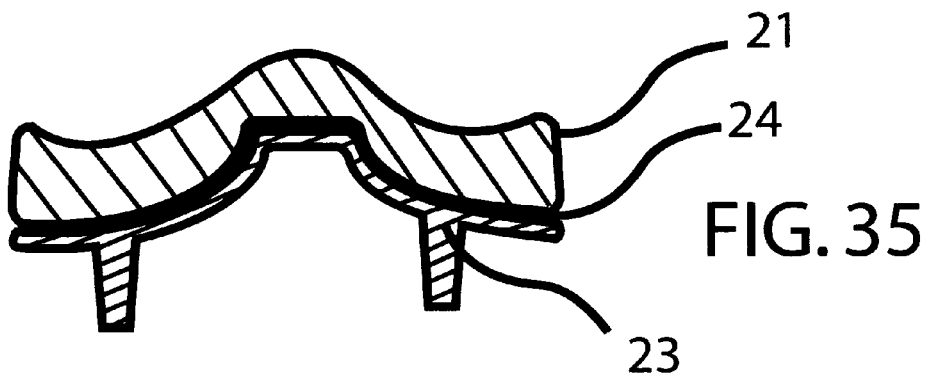
FIG. 35 shows the plan view of the ceramic fiber meniscus of FIG. 35 thermally bonded onto a metal prosthesis with a ceramic bonding material.

FIG. 34 shows the plan view and a sectional view of a flexibly compliant ceramic prosthetic meniscus [21] attached to a bone end [22] in an anatomical joint. FIG. 35 shows the plan view of a flexibly compliant ceramic prosthetic meniscus [21] thermally bonded onto a metal prosthesis [23] by means of a ceramic bonding material [24] prior to permanently attaching the metal prosthesis to the said bone end with bone glue.

Figure 36:
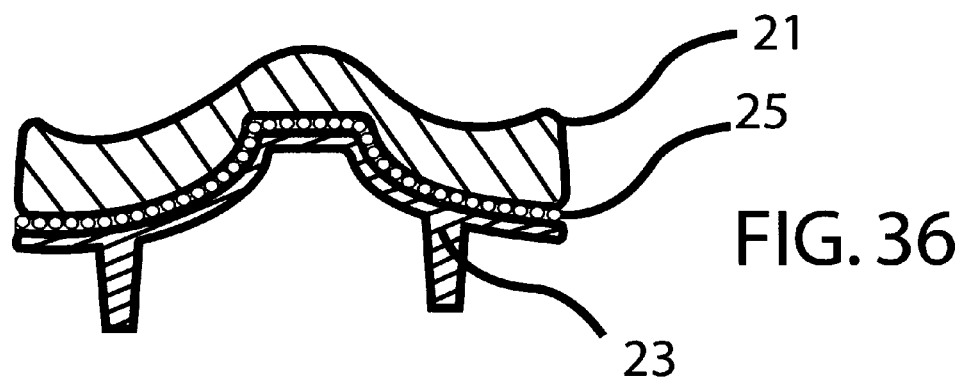
FIG. 36 shows the plan view of the ceramic fiber meniscus of FIG. 35 bonded onto a metal prosthesis with an epoxy.

FIG. 36 shows the plan view of a flexibly compliant ceramic prosthetic meniscus [21] attached to a metal prosthesis [23] by means of an epoxy [25] prior to permanently attaching the metal prosthesis to the said bone end with bone glue.

Figure 37:
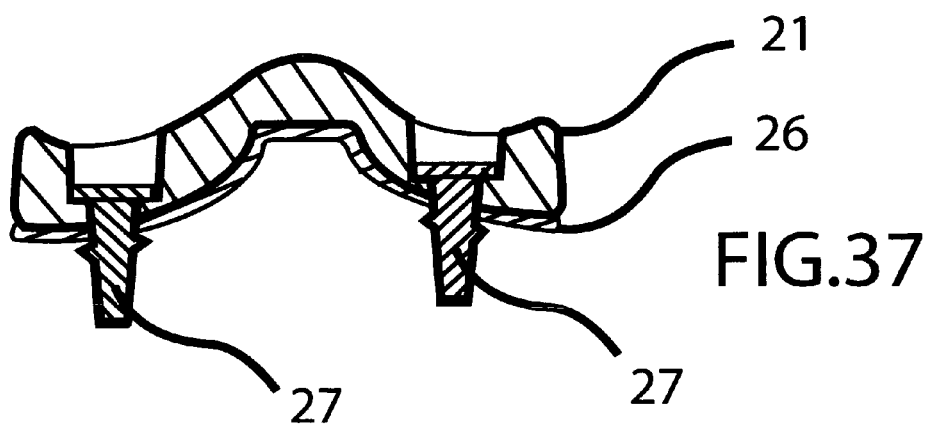
FIG. 37 shows the plan view of the ceramic fiber meniscus of FIG. 35 mounted onto a metal prosthesis with rivets.

FIG. 37 shows the plan view of a flexibly compliant ceramic prosthetic meniscus [21] attached to a metal prosthesis [26] by means of rivets [27] or other mechanical fasteners prior to permanently attaching the metal prosthesis to the said bone end with bone glue.

FIG. 38 shows the plan view and a sectional view of a flexibly compliant ceramic prosthetic meniscus [21] attached to a bone end [22] by means of sewing [28] the said flexibly compliant ceramic prosthetic meniscus to the tissues adjacent to the bone end.

FIG. 39 shows the plan view and a sectional view of a flexibly compliant ceramic prosthetic meniscus [21] attached to a bone end [22] by means of surgically placing the said flexibly compliant ceramic prosthetic meniscus [21] onto the bone end [22] in the anatomical joint and allowing the remaining cartilage tissue [29] to grow onto the said flexibly compliant ceramic prosthetic meniscus.

FIG. 40 shows the plan view and sectional view of an implantable ceramic fiber meniscus comprised of ceramic fibers formed into a rope-like structure [1] which is coiled into a pad configuration [2], with the proximal and distal ends [24] completely placed into the interior of the pad [2] to prevent damage to surrounding soft tissues.

Figure 41:
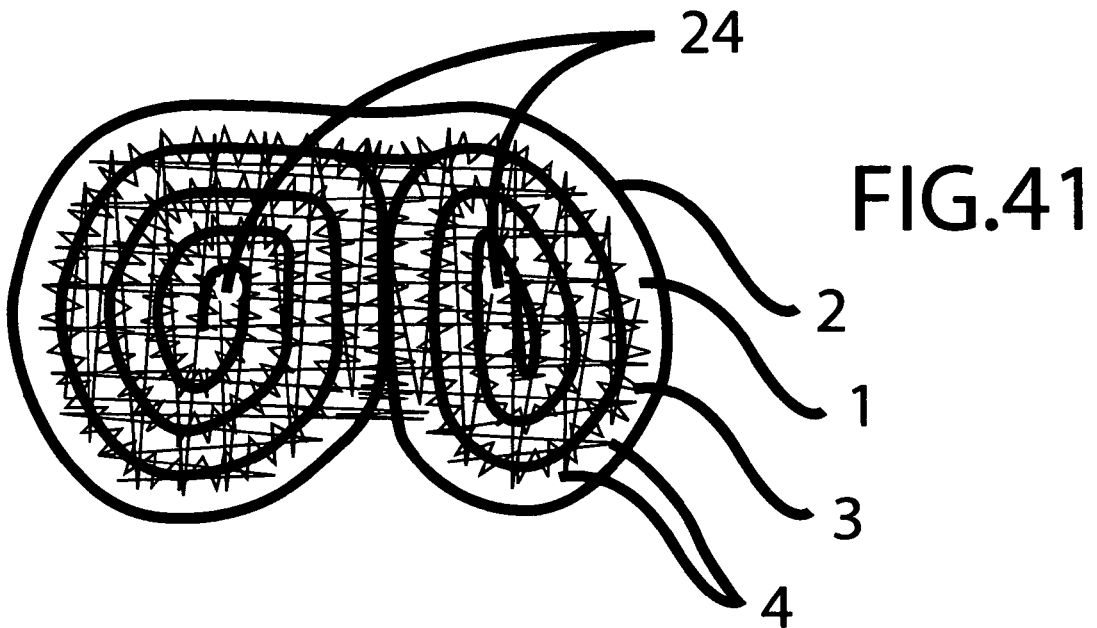
FIG. 41 shows the plan view of an implantable ceramic fiber meniscus pad of FIG. 40 which is sewn together.

FIG. 41 shows the plan view of the implantable ceramic fiber meniscus of FIG. 40 comprised of ceramic fibers formed into a rope-like structure [1] which is coiled into a pad configuration [2], with the proximal and distal ends [24] completely placed into the interior of the pad [2] to prevent damage to surrounding soft tissues, which is sewn together with zigzag stitches [3] and with multiple vertical and horizontal rows of stitches [4] using a high melting temperature ceramic thread to keep the pad from expanding laterally within the joint, so as to create a dimensionally stable and flexibly compliant ceramic prosthetic meniscus.

Figure 42:
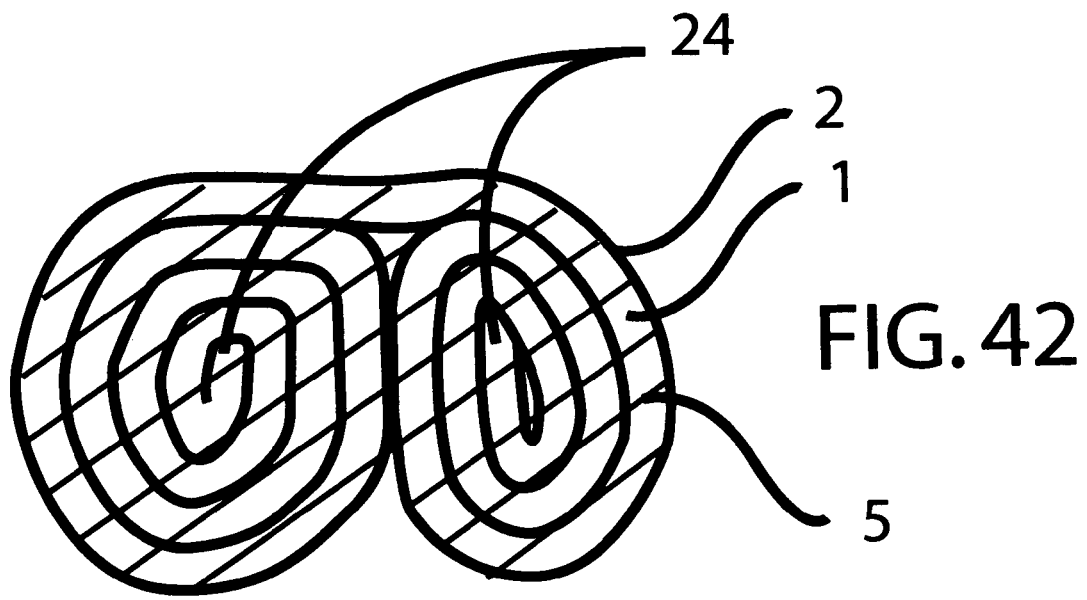
FIG. 42 shows the plan view of an implantable ceramic fiber meniscus pad of FIG. 40 which is thermally fused together.

FIG. 42 shows the plan view of the implantable ceramic fiber meniscus of FIG. 40 comprised of ceramic fibers formed into a rope-like structure [1] which is coiled into a pad configuration [2], with the proximal and distal ends [24] completely placed into the interior of the pad [2] to prevent damage to surrounding soft tissues, which is fixed together by being thermally fused [5] so as to create a dimensionally stable and flexibly compliant ceramic prosthetic meniscus.

Figure 43:
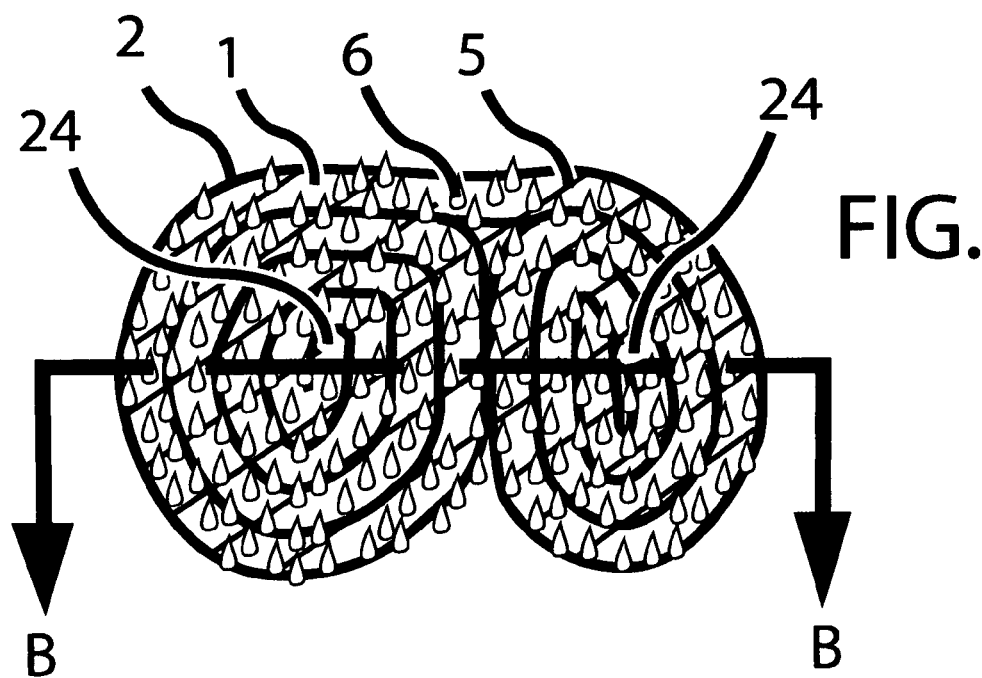
FIG. 43 shows a plan view of an implantable ceramic fiber meniscus pad of FIG. 40 which is coated with a ceramic material, and thermally fused together.

FIG. 43 shows the plan view of the implantable ceramic fiber meniscus of FIG. 40 comprised of ceramic fibers formed into a rope-like structure [1] which is coiled into a pad configuration [2], with the proximal and distal ends [24] completely placed into the interior of the pad [2] to prevent damage to surrounding soft tissues, which pad [2] has a coating made of a ceramic material [6], having a lower melting temperature than the ceramic fibers, which is melted and applied to the meniscus pad [2], and which meniscus pad [2] is fixed together by being thermally fused [5] so as to create a dimensionally stable and flexibly compliant ceramic prosthetic meniscus.

Figure 44:
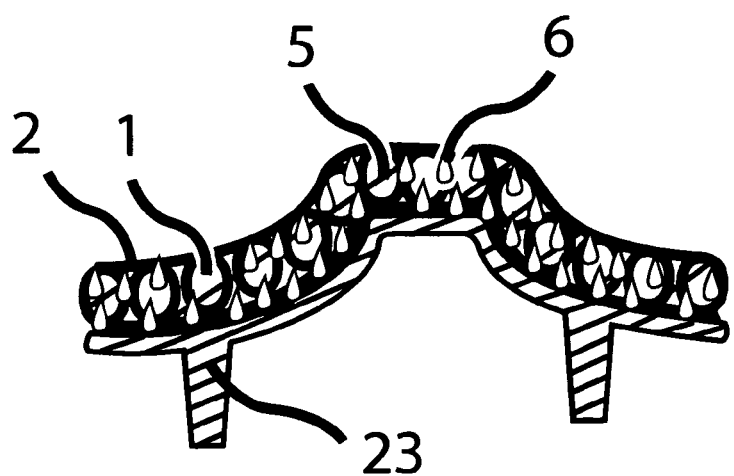
FIG. 44 shows a sectional view of an implantable ceramic fiber meniscus pad of FIG. 43 which is coated with a ceramic material, thermally fused together and thermally fused onto a metal prosthesis.

FIG. 44 shows sectional view B-B of the implantable ceramic fiber meniscus of FIG. 43 comprised of ceramic fibers formed into a rope-like structure [1] which is coiled into a pad configuration [2], with the proximal and distal ends [24] completely placed into the interior of the pad [2] to prevent damage to surrounding soft tissues, which has a coating made of a ceramic material [6], having a lower melting temperature than that of the ceramic fibers, which is melted and applied to the meniscus pad [2], which meniscus pad [2] is fixed together by being thermally fused [5], and which meniscus pad [2] is thermally fused [5] onto a metal prosthesis [23] of the patient's articulating joint.

Figure 45:
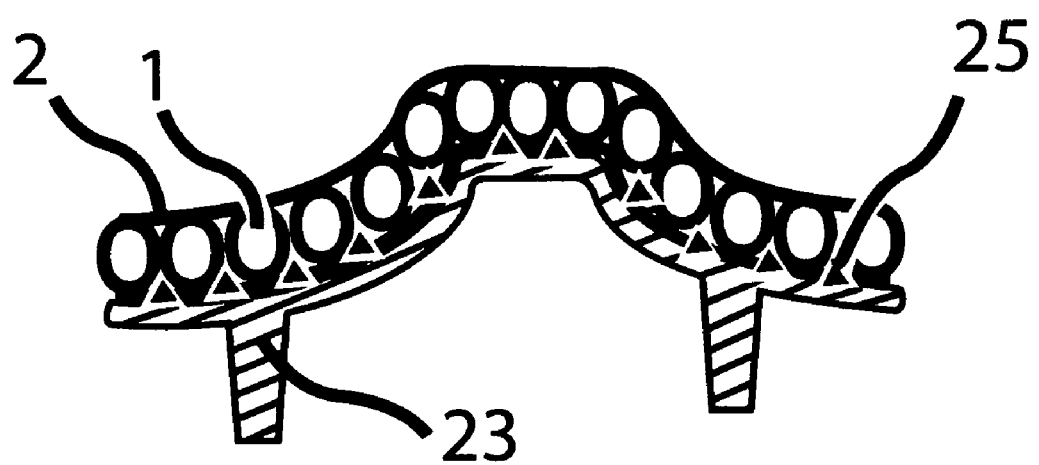
FIG. 45 shows the plan view of an implantable ceramic fiber meniscus pad of FIG. 40 which is bonded onto a metal prosthesis by means of an epoxy material.

FIG. 45 shows sectional view B-B of the implantable ceramic fiber meniscus of FIG. 44 comprised of ceramic fibers formed into a rope-like structure [1] which is coiled into a pad configuration [2], which pad is bonded onto a metal prosthesis [23] of the said patient's articulating joint by means of an epoxy material [25].

Because many varying and different embodiments may be made within the scope of the invention herein taught and because modifications may be made in the embodiment herein detailed in accordance with the descriptive requirements of the law, it is to be understood that details herein are to be interpreted as illustrative and not limiting.

What is claimed is:

1. An implantable meniscus for the repair or replacement of damaged cartilage in the orthopedic surgical repair of a patient's articulating joint comprising:
    flexible compliant ceramic fibers formed together into a rope-like structure, the rope-like structure having a proximal end, a distal end, and an outer surface extending along the proximal and distal ends,
    the rope-like structure is coiled into a pad configuration, wherein the proximal and distal ends of the structure are completely placed into an interior of the pad, said pad is fixed together so as to create a dimensionally stable, and flexibly compliant ceramic prosthetic meniscus and;
    wherein a section of the outer surface of the rope-like structure is abutting another section of the outer surface of the rope-like structure.

2. The implantable meniscus of claim 1, wherein said pad is fixed together by zigzag stitches and with multiple vertical and horizontal rows of stitches, using a high melting temperature ceramic thread, to join adjacent coils of said pad so as to create a more stabilized structure.

3. The implantable meniscus of claim 1, wherein said pad is fixed together by being thermally fused so as to create a more stabilized structure.

4. An implantable meniscus for the repair or replacement of damaged cartilage in the orthopedic surgical repair of a patient's articulating joint comprising:
    flexible compliant ceramic fibers formed together into a rope-like structure, the rope-like structure having a proximal end, a distal end, and an outer surface extending along the proximal and distal ends,
    the rope-like structure is coiled into a pad configuration, wherein the proximal and distal ends of the structure are completely placed into an interior of the pad, said pad is fixed together so as to create a dimensionally stable, and flexibly compliant ceramic prosthetic meniscus and;
    wherein a section of the outer surface of the rope-like structure is abutting another section of the outer surface of the rope-like structure and;
    wherein said pad is fixed together by zigzag stitches and with multiple vertical and horizontal rows of stitches using a high melting temperature ceramic thread to join adjacent coils of said pad so as to create a more stabilized structure and;
    wherein said meniscus comprises a coating made of a ceramic material having a lower melting temperature than said flexible compliant ceramic fibers, which said ceramic material coating is capable of being melted and being applied to the meniscus and;
    which said pad is thermally fused onto a metal prosthesis, to be used in the orthopedic surgical repair of the said patient's articulating joint, by means of said ceramic coating so as to create a more stabilized structure.

5. An implantable meniscus for the repair or replacement of damaged cartilage in the orthopedic surgical repair of a patient's articulating joint comprising:
    flexible compliant ceramic fibers formed together into a rope-like structure, the rope-like structure having a proximal end, a distal end, and an outer surface extending along the proximal and distal ends,
    the rope-like structure is coiled into a pad configuration, wherein the proximal and distal ends of the structure are completely placed into an interior of the pad, said pad is fixed together so as to create a dimensionally stable, and flexibly compliant ceramic prosthetic meniscus and:
    wherein a section of the outer surface of the rope-like structure is abutting another section of the outer surface of the rope-like structure and:
    wherein said meniscus comprises a coating made of an epoxy material, which said epoxy material is capable of being applied to said meniscus and:
    wherein said meniscus pad is bonded onto a metal prosthesis, to be used in the orthopedic surgical repair of the said patient's articulating joint, by means of epoxy material so as to create a more stabilized structure.

* * * * *